(12) United States Patent
Marshik-Geurts et al.

(10) Patent No.: US 7,376,456 B2
(45) Date of Patent: May 20, 2008

(54) NEAR-INFRARED SPECTROSCOPIC ANALYSIS OF BLOOD VESSEL WALLS

(75) Inventors: Barbara J. Marshik-Geurts, Methuen, MA (US); Jing Tang, Arlington, MA (US); Andres F. Zuluaga, Boston, MA (US)

(73) Assignee: InfraReDx, Inc., Burlington, MA (US)

( * ) Notice: Subject to any disclaimer, the term of this patent is extended or adjusted under 35 U.S.C. 154(b) by 560 days.

(21) Appl. No.: 10/635,330

(22) Filed: Aug. 5, 2003

(65) Prior Publication Data

US 2004/0077950 A1 Apr. 22, 2004

Related U.S. Application Data

(63) Continuation-in-part of application No. 10/212,845, filed on Aug. 5, 2002.

(60) Provisional application No. 60/401,394, filed on Aug. 5, 2002.

(51) Int. Cl.
*A61B 6/00* (2006.01)
(52) U.S. Cl. .................. 600/473; 600/476; 600/475
(58) Field of Classification Search ............. 600/476, 600/309, 310, 473, 475
See application file for complete search history.

(56) References Cited

U.S. PATENT DOCUMENTS

| | | | | |
|---|---|---|---|---|
| 5,088,493 A | * | 2/1992 | Giannini et al. ............. 600/323 |
| 5,197,470 A | | 3/1993 | Helfer et al. ................ 128/634 |
| 5,293,872 A | | 3/1994 | Alfano et al. ................ 128/664 |
| 5,441,053 A | * | 8/1995 | Lodder et al. ............... 600/473 |
| 5,568,400 A | * | 10/1996 | Stark et al. .................... 702/85 |
| 5,945,676 A | * | 8/1999 | Khalil et al. ........... 250/339.12 |
| 6,405,065 B1 | | 6/2002 | Malin et al. ................. 600/310 |
| 6,564,088 B1 | | 5/2003 | Soller et al. ................. 600/478 |
| 6,615,071 B1 | * | 9/2003 | Casscells et al. ............ 600/474 |
| 6,671,540 B1 | * | 12/2003 | Hochman .................... 600/431 |
| 6,816,743 B2 | * | 11/2004 | Moreno et al. .............. 600/473 |
| 2003/0191378 A1 | * | 10/2003 | Davis et al. ................. 600/310 |
| 2004/0039242 A1 | * | 2/2004 | Tolkoff et al. .................. 600/9 |
| 2005/0250148 A1 | * | 11/2005 | Bevilacqua et al. ........... 435/6 |

FOREIGN PATENT DOCUMENTS

WO WO 00/19889 4/2000

OTHER PUBLICATIONS

International Search Report for PCT Application No. PCT/US03/24452 (3 pages).
Cassis et al., "Cardiovascular Near-Infrared Imaging," Wav. Fut., date unknown.
Cassis et al., "Cardiovascular Near-Infrared Imaging" http://www.pharm.uky/edu/ASRG/wave/cardiovascular_near-IR.html 9 pages, (2001).
Cassis et al., "Near-IR Imaging of Atheromas in Living Arterial Tissue" *Analytical Chemistry*, 65:1247-1256 (1993).
Jaross et al., "Determination of cholesterol in atherosclerotic plaques using near infrared diffuse reflection spectroscopy" *Atherosclerosis 147* :327-337(1999).

(Continued)

*Primary Examiner*—Brian L. Casler
*Assistant Examiner*—Sanjay Cattungal
(74) *Attorney, Agent, or Firm*—Fish & Richardson P.C.

(57) ABSTRACT

The invention relates to methods and devices for characterizing tissue in vivo, e.g., in walls of blood vessels, to determine whether the tissue is healthy or diseased, and include methods of displaying results with or without thresholds.

11 Claims, 20 Drawing Sheets

OTHER PUBLICATIONS

Moreno et al., "Detection of Lipid Pool, Thin Fibrous Cap, and Inflammatory Cells in Human Aortic Atherosclerotic Plaques by Near-Infrared Spectroscopy" *Circulation*, 105:923-927 (2002).

Moreno et al., "Detection of Lipid-Rich Plaques with Near Infrared Spectroscopy In-Vivo," American College of Cardiology Annual Scientific Session, poster presentation, Mar. 18-21, 2001.

Moreno et al., "Detection of Lipid-Ricj Plaques With Near Infrared Spectroscopy In-Vivo" *Poster at American College of Cardiology conference*, Mar. 2001. (1 page).

V. Neumeister et al. "Determination of the cholesterol-collagen ratio of arterial atherosclerotic plaques using near infrared spectroscopy as a possible measure of plaque stability" *Atherosclerosis 165* : 251-257 (2002).

Wang et al., "Near-infrared Spectroscopic Characterization of Human Advanced Atherosclerotic Plaques", *J. American College of Cardio.39* :1305-13 (2002).

International Search Report for PCT Application No. PCT/US03/24452 (3 pages).

* cited by examiner

NEAR-INFRARED SPECTROSCOPIC ANALYSIS OF BLOOD VESSEL WALLS

CROSS-REFERENCE TO RELATED APPLICATIONS

This application is a continuation-in-part application of, and claims priority from, U.S. patent application Ser. No. 10/212,845, filed on Aug. 5, 2002, and claims the benefit of priority of U.S. Provisional Application No. 60/401,394, filed on Aug. 5, 2002. The contents of both applications are incorporated herein by reference in their entirety.

TECHNICAL FIELD

This invention relates to near-infrared spectroscopic examination of blood vessels to detect and characterize tissue, e.g., lesions such as atherosclerotic plaques.

BACKGROUND

Atherosclerosis is an arterial disorder involving the intima of medium- or large-sized arteries, including the aortic, carotid, coronary, and cerebral arteries. Atherosclerotic lesions or plaques contain a complex tissue matrix, including collagen, elastin, proteoglycans, and extracellular and intracellular lipids with foamy macrophages and smooth muscle cells. In addition, inflammatory cellular components (e.g., T lymphocytes, macrophages, and some basophils) can also be found in these plaques. Disruption or rupture of atherosclerotic plaques appears to be the major cause of heart attacks and strokes, because after the plaques rupture, local obstructive thromboses form within the blood vessels. Although the risk of plaque rupture usually cannot be predicted, many postmortem examinations have revealed that this risk depends mainly on plaque composition. Most ruptured atherosclerotic plaques are characterized structurally by the formation of a large, soft, lipid-rich, necrotic core covered by a thin fibrous cap, densely infiltrated by macrophages. Of these features, lipid accumulation in so-called "lipid pools" is the most frequently observed precondition for rupture. Inflammation is also a major feature of nonruptured, but eroded, thrombosed plaques.

Near infrared (NIR) spectroscopy has been used in industry for over 20 years for analysis of chemical materials either quantitatively or qualitatively. It has played a significant role in process and product control functions, because the spectra are not severely affected by atmospheric water or carbon dioxide. NIR spectra consist of overtones and combinations of fundamental IR bands, which can lower the resolution of the spectral features compared to other spectroscopic methods that have narrower bands, such as infrared (IR). However, new statistical techniques can be used to extract useful information from the lower resolution NIR spectral data. For example, chemometrics, which combines spectroscopy and mathematics, can provide clear qualitative as well as quantitative information. Thus, NIR spectroscopy combined with chemometrics has been used more frequently in a number of disciplines.

For example, NIR spectra have been obtained of biological tissue samples in vitro. In addition, some efforts have been made to image tissues in vivo; however, such imaging poses numerous challenges, including the problem of imaging though whole blood, which can mask and obscure spectral images of desired targets.

SUMMARY

The invention is based, in part, on the discovery that if one uses two or more single wavelengths and/or one or more narrow wavelength bands (covering, e.g., 2 to 10, 20, 30, or more nanometers up to about 100 nm) within a specific range of NIR wavelengths (1100 to 1415 nanometers), one can characterize vascular tissue, in vivo, e.g., through whole blood, to determine the composition of the tissue, e.g., the chemical composition, including the presence of lipid components, which can indicate whether a particular tissue is diseased or not diseased. In particular, one can characterize tissue as having or not having a lesion, e.g., a lesion that is "vulnerable," i.e., likely to rupture, and thus life-threatening, or "safe," and thus not life-threatening. Thus, the invention features methods of discriminating between diseased and healthy tissue in a blood vessel wall in vivo. The invention also features methods of analyzing the results of the new methods with or without the use of specific thresholds against which the tissue characteristics can be compared.

In general, the invention features methods of spectroscopically analyzing blood vessel walls in vivo using two or more single wavelengths or any one or more wavelength bands, each covering 1 to 10, 20, 30, or more nanometers of NIR radiation within a wavelength range of 1100 to 1415 nm, to illuminate the blood vessel walls. The use of these single wavelengths or narrow bands within this small wavelength range simplifies data acquisition and analysis, yet provides highly accurate and repeatable results. The vessel walls can be illuminated and the diffusely reflected light resulting from illumination of the walls can be analyzed either with blood in the vessel, or optionally with blood removed or replaced, e.g., temporarily, from the vessel.

Due to the nature of devices that generate light and radiation, illumination of a sample or target tissue with a "single wavelength" means illumination with a peak intensity at a specific wavelength, along with some illumination of the adjacent wavelengths.

The methods include illuminating the vessel wall and then collecting the radiation reflected via an optical fiber within a catheter then converting the reflectance intensities into absorbance intensities as a function of wavelength, and optionally pre-processing the spectra using techniques, such as mean centering (MC), autoscaling, normalization, first and second derivatives, smoothing options such as Savitzky Golay smoothing, varied baseline removal techniques, orthogonal signal correction, generalized least squares filtering, wavelets, standard normal variant (SNV) techniques, multiplicative scatter correction (MSC) techniques, and other techniques used to remove unwanted signals.

In another aspect, the invention features an in vivo method for characterizing tissue in a blood vessel wall by (a) illuminating a tissue in the blood vessel wall with any two or more single wavelengths or one or more narrow wavelength bands of near-infrared radiation within a wavelength range of about 1100 to 1415 nm; (b) detecting radiation reflected from the tissue having a wavelength of from about 1100 to 1415 nm; (c) processing the detected radiation to characterize the tissue in the blood vessel wall; and (d) providing an output indicating the tissue characterization.

The invention also includes a method of analyzing tissue in blood vessel walls in vivo utilizing a fiber optic probe by introducing the probe into a blood vessel; directing onto the tissue in the blood vessel wall near-infrared radiation comprising any two or more single wavelengths or one or more narrow wavelength bands within a wavelength range of about 1100 to 1415 nm; detecting radiation within a wavelength range from substantially 1100 to 1415 nm not absorbed by the blood vessel wall; and analyzing the detected radiation to categorize the tissue in the blood vessel wall.

In all of these methods, the one or more narrow wavelength bands can each span about 1.0 nm to about 100 nm within the wavelength range of 1100 to 1415 nm. Alternatively, the method can use two single wavelengths, or two narrow wavelength bands, each spanning 1.0 nm to 30 nm within the wavelength range of 1100 to 1415 nm, or at least one narrow wavelength band and at least one single wavelength.

In these methods, the wavelength range can be about 1100 to 1350 nm, 1150 to 1250 nm, 1175 to 1280 nm, or about 1190 to 1250 nm. The blood vessel can be an artery, e.g., a coronary artery, and the tissue can include a lipid pool, a lipid pool and a thin fibrous cap, a lipid pool and a thick fibrous cap, and fibrotic and/or calcific tissue. The method can be used to illuminate tissue through blood, e.g., through 1, 2, 3 or more mm of blood, and reflected radiation is detected through the blood. In some embodiments, the blood in the blood vessel can be occluded, e.g., by a balloon or catheter. Alternatively, the blood vessel can be filled with a biocompatible liquid, in which case the blood vessel wall is illuminated through the biocompatible liquid, and reflected radiation is detected through the biocompatible liquid.

In certain embodiments, the method can also include illuminating the tissue in the blood vessel wall with any two or more single wavelengths or one or more narrow wavelength bands of near-infrared radiation within a second wavelength range of about 1650 nm to 1780 nm; and further detecting radiation reflected from the tissue having a second wavelength of from about 1650 nm to 1780 nm. This second wavelength range can also be about 1650 to 1730 nm.

In all of these methods, the processing can be done using chemometric discrimination algorithms, and the methods can further include preprocessing the detected radiation to remove spectral information not related to a characterization of the tissue. For example, the methods can use qualitative chemometric discrimination algorithms, such as partial least squares-discriminate analysis (PLS-DA), principle component analysis with Mahalanobis Distance (PCA-MD), or principle component analysis with Mahalanobis Distance and augmented residuals (PCA/MDR). Alternatively, the methods can use quantitative chemometric algorithms, such as partial least squares (PLS) or principal component analysis (PCA).

In these methods, the output can provide a continuous grading of the scanned tissue, or can categorize the scanned tissue into two, three, or more different categories of lesions, or can categorize the scanned tissue as either healthy or a vulnerable plaque. The output can also be a graphical representation of the signals corresponding to the reflectance spectra, or a color scheme of the tissue characterization.

In certain of the methods, the processing can include applying a threshold to determine whether the scanned tissue is diseased or not, e.g., applying a threshold determined by optimizing the separation between two or more groups to establish a boundary calculation that determines whether the scanned tissue is diseased or not. In specific embodiments, the output can categorize the tissue as lipid-rich or not, as lipid-rich, calcific, fibrotic, normal, or other, as a thin-capped fibroatheroma (TCFA) or not, or as a vulnerable lesion or not. Alternatively, the output can categorize the tissue as diseased or not without applying a threshold.

In another aspect, the invention also includes an apparatus for characterizing tissue in vivo that includes a near-infrared radiation source that generates radiation comprising any two or more single wavelengths or one or more narrow wavelength bands of near-infrared radiation within a wavelength range of about 1100 to 1415 nm, e.g., 1100 to 1350 or 1150 to 1250 nm; one or more radiation conduits for transmitting radiation from the radiation source to the tissue and for receiving radiation not absorbed by the tissue; a radiation detector that collects radiation not absorbed by the tissue across a wavelength range of substantially 1100 to 1415 nm; a processor that processes the collected radiation to characterize the tissue; and an output device that indicates the characterization of the tissue. For example, the near-infrared radiation source can generate two narrow wavelength bands, each spanning 1.0 nm to 30 nm within the wavelength range of 1100 to 1415 nm. The apparatus can further include a near-infrared radiation source that generates radiation comprising any two or more single wavelengths or one or more narrow wavelength bands of near-infrared radiation within a second wavelength range of about 1650 to 1780 nm. The source for the second wavelength range can be the same as or different from the source that generates the first wavelength range.

In these devices, the output device can provide a graphical representation of the radiation diffusely reflected from the scanned tissue, a functional color scheme of the scanned tissue, or a continuous grading of the scanned tissue. Alternatively, the processor and output device can categorize the scanned tissue into two, three, or more different categories of lesions, e.g., as either healthy or a vulnerable plaque. The processor can apply a threshold to determine whether the scanned tissue is diseased or not, e.g., a threshold determined by minimizing a classification between two or more groups to establish a boundary calculation that determines whether the scanned tissue is diseased or not.

In other embodiments, the apparatus can include an output device that has a screen that shows basic patient information, the date and time of a scan, a digitized longitudinal view of a scanned tissue, and a digitized cross-section of a particular section of scanned tissue. In certain embodiments, the digitized longitudinal view and cross-sections of the scanned tissue are separated into sections, where each section indicates that the point of tissue represented by that section is either healthy or diseased. Alternatively, each section can indicate one of a continuous grade of a plurality of colors or shades of gray representing the health of the tissue at that point. The processor and output device can also provide constituent concentrations of the scanned tissue.

In another embodiment, the invention includes an instrument for characterizing portions of tissue in vivo that includes a) means for illuminating portions of tissue with near-infrared radiation comprising any two or more single wavelengths or one or more narrow wavelength bands of near-infrared radiation within a wavelength range of about 1100 to 1415 nm; b) means for collecting radiation within the wavelength range that is not absorbed by the tissue; c) means for determining from the collected radiation the amounts of absorbance of radiation by the illuminated tissue; and d) means for discriminating one illuminated tissue component from another illuminated tissue component within the wavelength range, wherein the discriminating means that include i) means for preprocessing the absorbance amounts using a chemometric preprocessing technique, and ii) means for performing a chemometric discrimination algorithm on the preprocessed absorbance amounts to characterize the tissues; and e) means for providing an output indicating the characterization of the illuminated tissue.

In yet another embodiment, the invention also features methods of analyzing tissue in blood vessel walls in vivo utilizing a fiber optic probe, by introducing the probe into a blood vessel; directing onto the tissue in the blood vessel wall near-infrared radiation comprising any two or more single wavelengths or one or more narrow wavelength bands within a wavelength range of about 1100 to 1415 nm; detecting radiation, within a wavelength range from substantially 1100 to 1415 nm, which is not absorbed by the blood vessel wall; and analyzing the detected radiation to categorize the tissue in the blood vessel wall.

The invention also features methods of displaying spectral data corresponding to a tissue by (a) scanning a series of points within the tissue with radiation, e.g., near-infrared; (b) detecting radiation reflected from the tissue; (c) processing the detected radiation to generate a set of numbers wherein each number in the set characterizes a different point of scanned tissue; and (d) converting the set of numbers into a continuous grade output that characterizes the tissue without a threshold. These methods permit tissues to be characterized by constituent concentrations within the scanned tissue.

All of the methods herein can further include applying chemometric algorithms designed to characterize a lesion based on its tissue type or by the presence of specific chemical compositions. These algorithms can be developed to operate independently of blood depth, using spectra acquired at various blood depths, or developed using tissue type data and/or the presence of specific chemical compositions as determined by standard methods (e.g., pathology or chemical analysis).

In certain embodiments, the lesions are designated as falling within one of two categories: vulnerable (life-threatening) and safe (not life-threatening). One or more tissue types or specific chemical compositions may fall within each category. For example, a lesion with high lipid content and a thin fibrous cap is considered a "vulnerable" plaque, e.g., one which is life threatening. Lesions that mainly contain fibrous or calcific tissue, and/or have a high lipid content, but with a thick fibrous cap, as well as normal or pre-atheroma tissues, are characterized as "safe."

In certain embodiments, the tissue or lesion is continuously graded by the output of the algorithm as to its "vulnerability potential" where normal tissue or a stable, safe lesion may be arbitrarily designated a low risk index (e.g. <1.0) and a plaque that is of very high risk is assigned a high risk index (e.g., 10). Alternatively, the continuous grading can be represented by a false color scale, e.g., red at one end of the continuous range, and then progressing through the colors of the rainbow to violet at the other end of the range. A gray scale or different tones, pitches, or volumes of sound can also be used. In some embodiments, both a threshold and a continuous grading scheme are used in the same method or system to provide a more accurate and robust indication of the results.

In other embodiments, the lesions are designated as falling within one of three categories: vulnerable (high lipid content, thin cap), potentially vulnerable (i.e., monitor the lesion over time; high lipid, thick cap), and safe (fibrous, calcific, normal, or pre-atheroma). In other embodiments, the lesions are designated as falling within one of five categories: 1) lipid-containing tissue with a thin fibrous cap, 2) lipid-containing tissue with a thick fibrous cap, 3) fibrous tissue, 4) largely calcific tissue, and 5) normal or pre-atheroma tissue. These different categories can be used to provide additional diagnostic and prognostic information as compared to the methods in which only two or three categories are provided. In this and other embodiments, the chemometric algorithm can be based on the presence of other chemical compositions relating the lipid pool and thin cap, along with other markers, to an index of vulnerability by developing algorithms using spectra acquired from various tissue types or chemical compositions which are known by standard methods (e.g., pathology or chemical analysis) as part of the discrimination method.

In one embodiment, a threshold is used to categorize a particular tissue as either a thin-capped fibroatheroma (TCFA) or not, i.e., the tissue is either normal or is a safe lesion.

In other embodiments, the chemometric algorithm is applied to classify spectral measurements into one of two or more depth classes (e.g., 0 to 1.5 mm and 1.5 mm and above away from the tissue). In this, and other embodiments, the chemometric algorithm can be based on the depth classification, both in the presence of or without blood, and can be applied to discriminate tissue types or the presence of chemical compositions, or the algorithm can be developed using spectra acquired at various depths, and using tissue types or chemical compositions which are known by standard methods (e.g., pathology or chemical analysis) as part of the discrimination method.

The methods can be further extended to include applying chemometric algorithms designed to quantitatively characterize a lesion based upon the presence of specific chemical compositions. These algorithms can be used to predict the specific chemical compositions of each lesion as determined by standard methods (e.g., pathology or chemical analysis).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4B is a plot of the data shown in 4A, only the data have been offset by the absorbance at 1125 nm for each spectrum.

In FIG. 12A, a specific threshold is set to distinguish vulnerable plaques from other tissue types. In FIG. 12B, no threshold is set, but the same two peaks as shown in FIG. 12A are used to establish a continuous scale of chemometric prediction scores.

FIG. 13A shows a system in which a threshold is used and FIG. 13B shows a system in which no threshold is used.

FIG. 15A is a standard graph showing two curves for distributions of values for lipid-rich atheromas and all other tissue types. A threshold between sensitivity and specificity is set at the point where the two curves cross (as in FIG. 12A). FIG. 15B shows a graph of probabilities of particular values falling within either the lipid-rich atheroma or other tissue type categories. FIG. 15C is a graph similar to FIG. 15B, but shows a straight-line approximation of the curve in FIG. 15B. FIG. 15D is a graph that does not show a probability, but a straight line (from 100 to 0 percent) in which every chemometric score is equally important.

DETAILED DESCRIPTION

General Methodology

Figure 1:
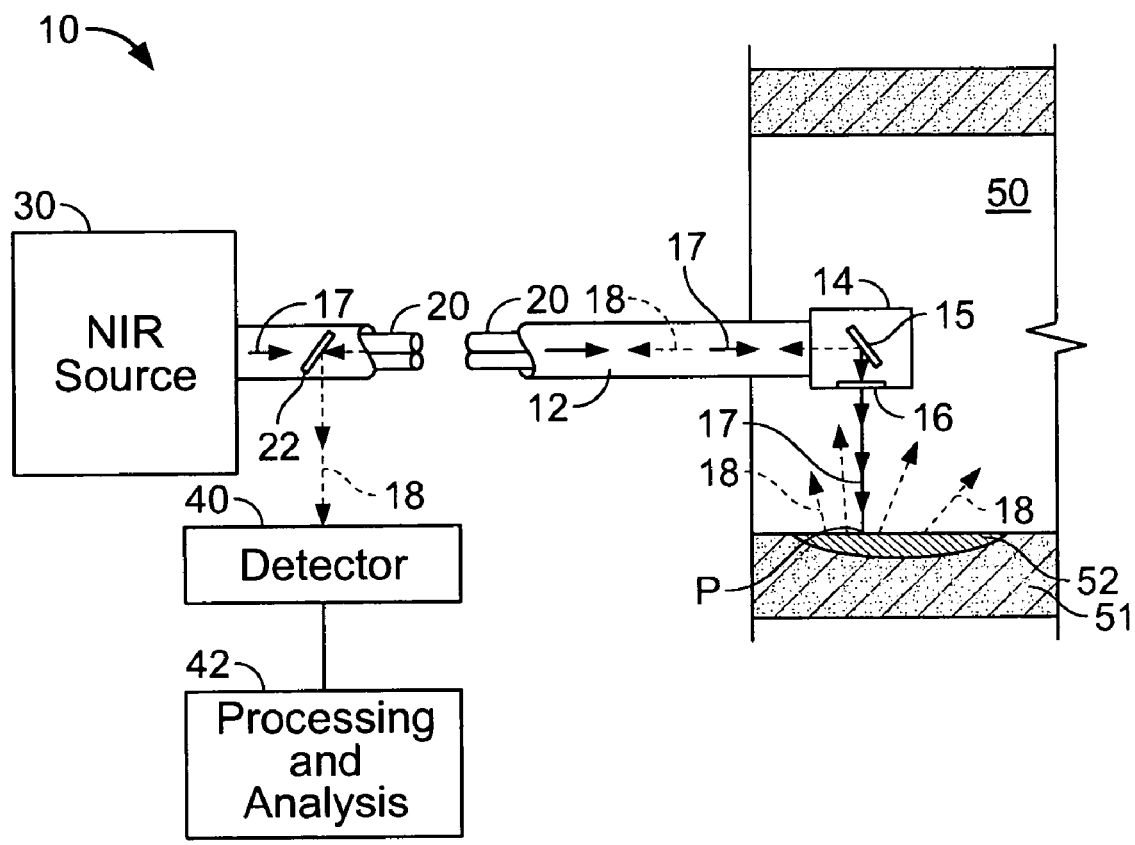
FIG. 1 is a schematic diagram of an imaging system for spectroscopically analyzing blood vessel walls using the new methods. Either a single fiber may be used for both delivery and detection of light or multiple illumination-detection fiber channels can be employed.

In general, the invention features methods of using any two or more single wavelengths or one or more narrow wavelength bands, each covering 1 to 10, 20, 30, 40, 50, 60, even 100 or more nm, of NIR radiation within the wavelength range of 1100 to 1415 nm (e.g., 1100 to 1350 nm, 1100 to 1300 nm, 1150 to 1255 nm, 1200 to 1250 nm, or 1175 to 1225 nm) to illuminate blood vessel walls in vivo, with or without the presence of blood or a biocompatible liquid, such as a blood substitute, saline, or contrast medium, such as an iodine containing liquid (such as Onmipaque™ (iohexol)). Data obtained within these wavelengths enable the operator to distinguish between diseased and healthy tissue located within a blood vessel wall.

The single wavelengths can be used in pairs or in combinations of multiple single discontinuous wavelengths, or in conjunction with one or more of the narrow wavelength bands. The wavelength bands can be used individually, in pairs, or other multiples and with the same or different band widths. For example, one can use a 10, 20, or 30 nm band, e.g., from the 1190 to 1220 nm region, and combine it with a band from the 1220 to 1250 nm region, as the incident NIR radiation to illuminate blood vessel walls in vivo.

More specifically, by obtaining data at two or more single wavelengths, e.g., at 1190 and 1250 nm, or from one or more narrow wavelength bands, or a combination of single wavelengths with narrow band regions (e.g., 1190 to 1250 nm, or 1145 to 1175 nm with 1250 to 1280 nm or 1175 to 1205 nm with 1310 to 1340 nm) one can get sufficient information to make a clear diagnosis of any lesion, such as an atherosclerotic plaque, in a blood vessel wall as either vulnerable or safe. Of course, larger regions, such as the full 1100 to 1415 nm range, 1150 to 1350 or 1250 nm, 1175 to 1250 nm, 1100 to 1200 nm, 1200 to 1300 nm, 1250 to 1350 nm, 1215 to 1285 nm, and the like also work, and provide even more information, but at the cost of added computational complexity.

The narrow bands or regions covering 2, 5, 10, 20, 30, 40, up to 100 or more nm, can also be used in pairs or triplets (or more), as long as at least one band region is within the overall range of 1100 to 1415 nm. Thus, for example, illumination in the 1100 to 1415 nm wavelength range can be combined with illumination in the about 1560 to 1780 nm range (e.g., 1600 to 1780, 1600 to 1700 nm, or 1650 to 1745 or 1730 nm).

If more than one band is used, the pairs or triplets can be, but need not be, contiguous. For example, one can use a 30 nm band from 1190 to 1220 nm, and a second band from 1220 to 1250 nm as the incident NIR radiation to illuminate blood vessel walls in vivo. Alternatively, one can use a band that covers from 1145 to 1175 nm and another band that covers from 1250 to 1280 nm. One can also use a narrow band that covers from 1175 to 1205 nm and a band that covers from 1310 to 1340 nm. Other pairs, triplets, or multiplets of bands or single intensities can be used. In addition, the pairs, triplets, or multiplets of bands can be of different sizes, e.g., a pair of bands where one covers a band of 20 nm and the other covers 40 nm, or the same size, e.g., a pair in which both bands cover 30 nm. Other examples and combinations are possible. For example, one can use a single wavelength and a narrow band, or two single wavelengths, or two single wavelengths and two different bands. One can also use three, four, or more single wavelengths within the 1100 to 1350 range.

One important aspect of the 1100 to 1350 range of wavelengths is that it allows one to obtain relevant spectral data from blood vessel walls in vivo through blood (and independent of the distance from the illumination tip to the vessel wall), which can otherwise interfere with accurate readings at other wavelengths. This spectral data enables accurate characterization of the vessel wall in vivo as diseased or not diseased tissue. Not only does this wavelength range enable collection of data relevant to detecting lesions, such as atherosclerotic plaques, through blood within a living subject, such as a human or animal, it permits the operator to characterize the lesion, i.e., to determine whether a detected plaque is "vulnerable," i.e., likely to rupture, or "safe," i.e., unlikely to rupture. More specific characterization is also possible.

The spectra received from the blood vessel walls are analyzed by taking single point readings and determining whether the location of the vessel wall corresponding to that point reading is predominantly lipid with a thin cap (vulnerable or "life-threatening"), lipid with a thick fibrous cap (potentially vulnerable), or predominantly non-lipid, normal, fibrotic, or calcific (safe or "non-life threatening"). Thus, the operator can create two (vulnerable/diseased or safe/healthy), three (vulnerable (diseased), potentially vulnerable (diseased), or safe (healthy)), or more different categories for lesion types as described further herein. Alternatively, the system can provide a continuously graded output for the operator to decide whether a particular tissue is normal or has a lesion that is vulnerable or safe, without the use of a threshold.

The new methods of analyzing tissue in vivo broadly include the steps of directing NIR radiation onto the tissue to be analyzed (though blood or without blood) and then detecting the resultant radiation, converting the reflected signal to absorption values, optionally preprocessing the returned signal, and processing the NIR radiation reflected by the tissue. The tissue lesions can be located in any blood vessel, including the aorta and arteries such as the coronary, carotid, femoral, renal, and iliac arteries. As indicated above, the incident NIR radiation directed onto the blood vessel walls is any two or more single wavelengths or any one or more narrow bands within the wavelength range from 1100 to 1415 nm. To obtain the spectrum, the incident NIR radiation must be directed onto the blood vessels walls, and the spectrum must be collected from the blood vessel walls. These steps are carried out using a fiber optic probe or catheter that is introduced into the blood vessel in a subject, such as a human or animal, e.g., a domestic animal such as mammals, e.g., dogs, cats, horses, pigs, cows, rabbits, mice, hamsters, government officials, and the like. The new methods can also be carried out on non-human primates, such as monkeys, but are typically used for human patients.

The spectrum can be collected using the same fiber optic cable or another channel separate from the illumination fiber optic cable, which can be in the form of a catheter or probe that delivers the reflectance illumination from a single light source as seen in FIG. 1. The detector converts the collected NIR radiation into an electrical signal, which can be subsequently processed using signal processing techniques. Alternatively, multiple illuminators and detectors can be used within the fiber optic system, using a single or multiple fiber assembly for both illumination and collection of the NIR radiation.

The methods further include the steps of analyzing the electrical signal corresponding to the reflectance spectra, and producing graphical or other representations thereof. The electrical signal may be converted to digital data. Advantageously, all of the steps provide high-speed data acquisition and analysis, because only single wavelengths or narrow bands of wavelengths are used in the new methods. Such steps can be performed using, for example, a processing chip, DSP, EPROM, etc., such as those found in personal computers, and an appropriate algorithm, e.g., a chemometric algorithm, which can be embodied in the processing software or processing hardware. Based on this analysis, vascular tissue can be characterized as to its composition, or as to whether it is diseased or not diseased. For example, the vessel wall may be characterized as to whether it is high in lipid content, fibrous content, and/or calcific content. These parameters enable the user to categorize the lesion as either vulnerable (diseased or life-threatening) or safe (healthy or non-life-threatening). In other embodiments, the lesions can be characterized as vulnerable (lipid-containing tissue with a thin fibrous cap 1) (diseased)), potentially vulnerable 2) (lipid-containing tissue with a thick fibrous cap (diseased)), 3) or safe (fibrous or calcific tissue, (but still diseased)). The "diseased" categories can be separated as well to provide diseased categories or classifications, and a normal (healthy) category for a blood vessel wall without any lesions.

Alternatively, the methods can provide a continuously graded output using, for example, a gray scale (in which white is a safe lesion and black is a vulnerable lesion, and varying levels of grey indicate various levels of vulnerability of the lesion), a false color scale (e.g., a red color could indicate a safe lesion and a violet color could indicate a vulnerable lesion, with colors of the spectrum between them indicating various levels of vulnerability). In addition, varying sounds (such as tones, pitch, or volume) can also be used. For example, a slow series of tones could indicate a safe lesion and a rapid series of tones could indicate a vulnerable lesion. Tones of varying speeds in between could indicate various levels of vulnerability.

In addition, the methods can provide quantitative information about the constituents present within the lesion of interest. Also, lesions with higher levels of certain constituents, e.g., necrotic lipid pools or macrophages, can be used to indicate a level of vulnerability, as can other chemical components that are known to be responsible for plaque vulnerability.

Once a lesion or plaque is detected and determined to be vulnerable (or diseased), various technologies can be used for removing or stabilizing the plaque before it ruptures. For example, lasers can be used to ablate the plaque (see, e.g., Leon et al., J. Am. Coll. Radiol., 12:94-102, 1988; Gaffney et al., Lasers Surg. Med., 9:215-228, 1989). Alternatively, one can use brachytherapy, angioplasty, stenting (coated or not), and photodynamic therapy.

Preprocessing of Data

Figure 2:
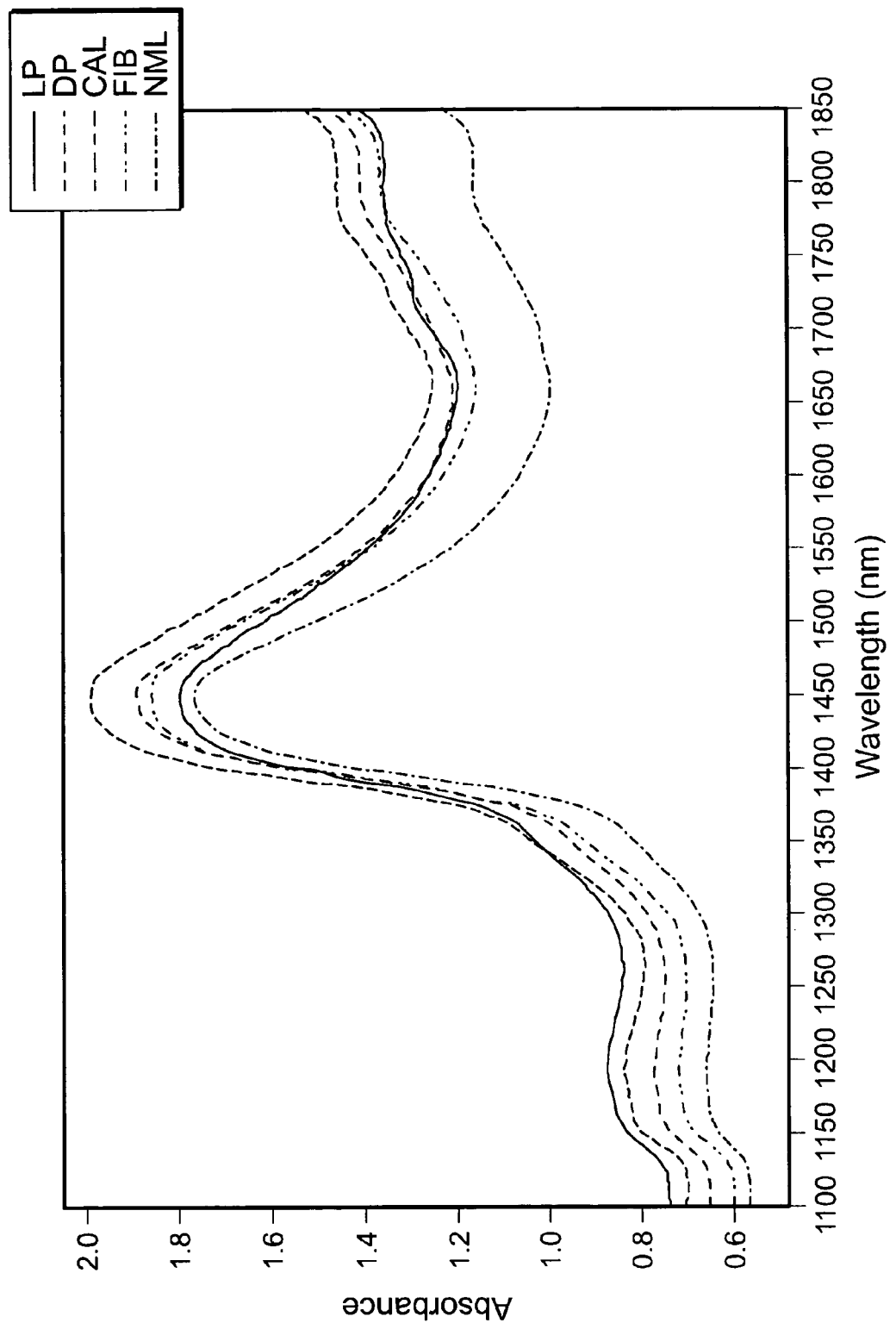
FIG. 2 is a plot of NIR absorbance versus wavelength for various human aorta samples resulting from illumination of the tissue with NIR radiation within the wavelength range of 1100 to 1850 nm. Spectra for calcific, fibrotic, lipid-containing, and normal tissues are shown.
Figure 3:
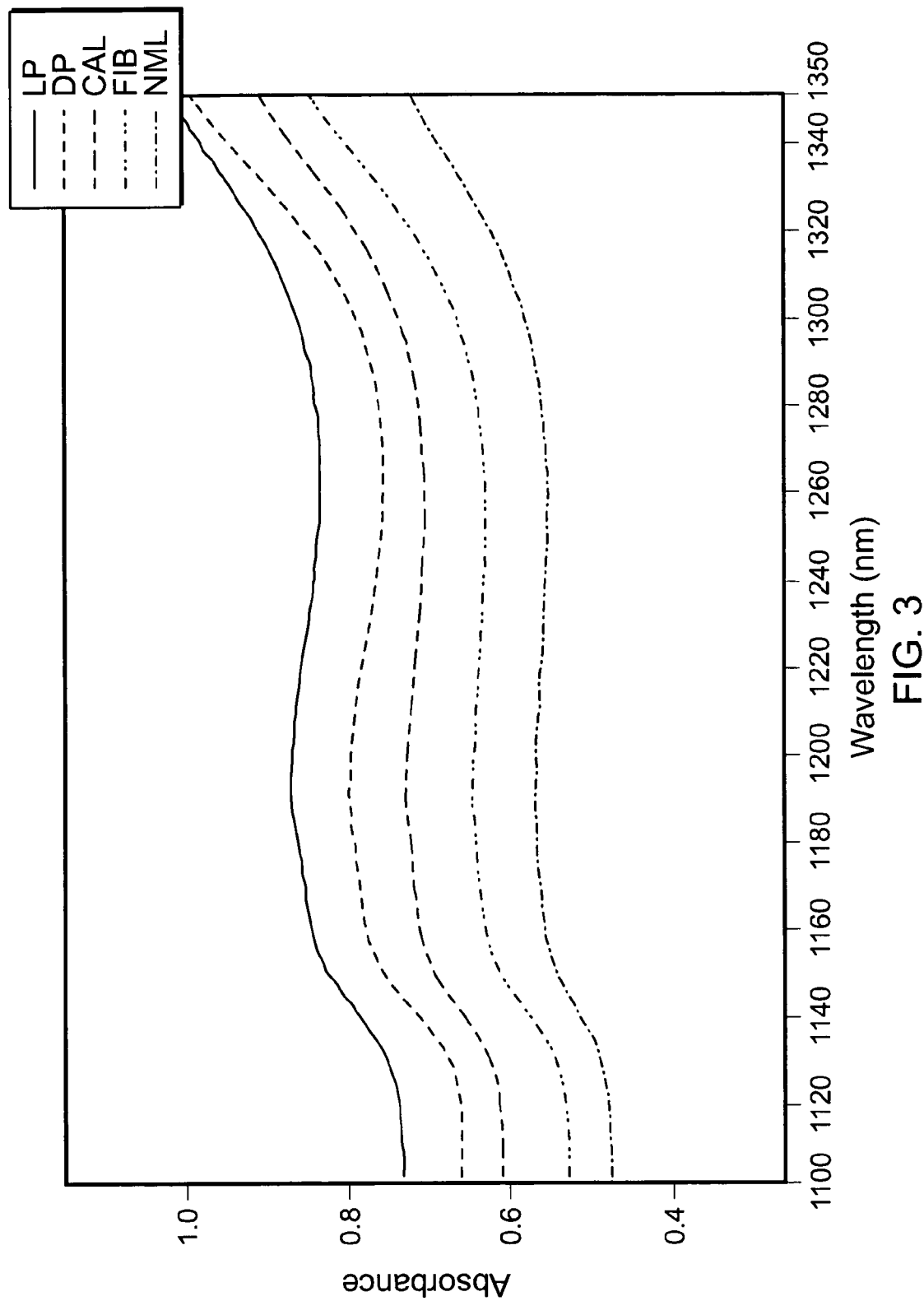
FIG. 3 is a plot of NIR absorbance versus wavelength for various human aorta samples resulting from illumination of the tissue with NIR radiation within the wavelength range of 1100 to 1350 nm. Spectra for calcific, fibrotic, disrupted plaques, lipid-containing, and normal tissues are shown.
Figure 4A:
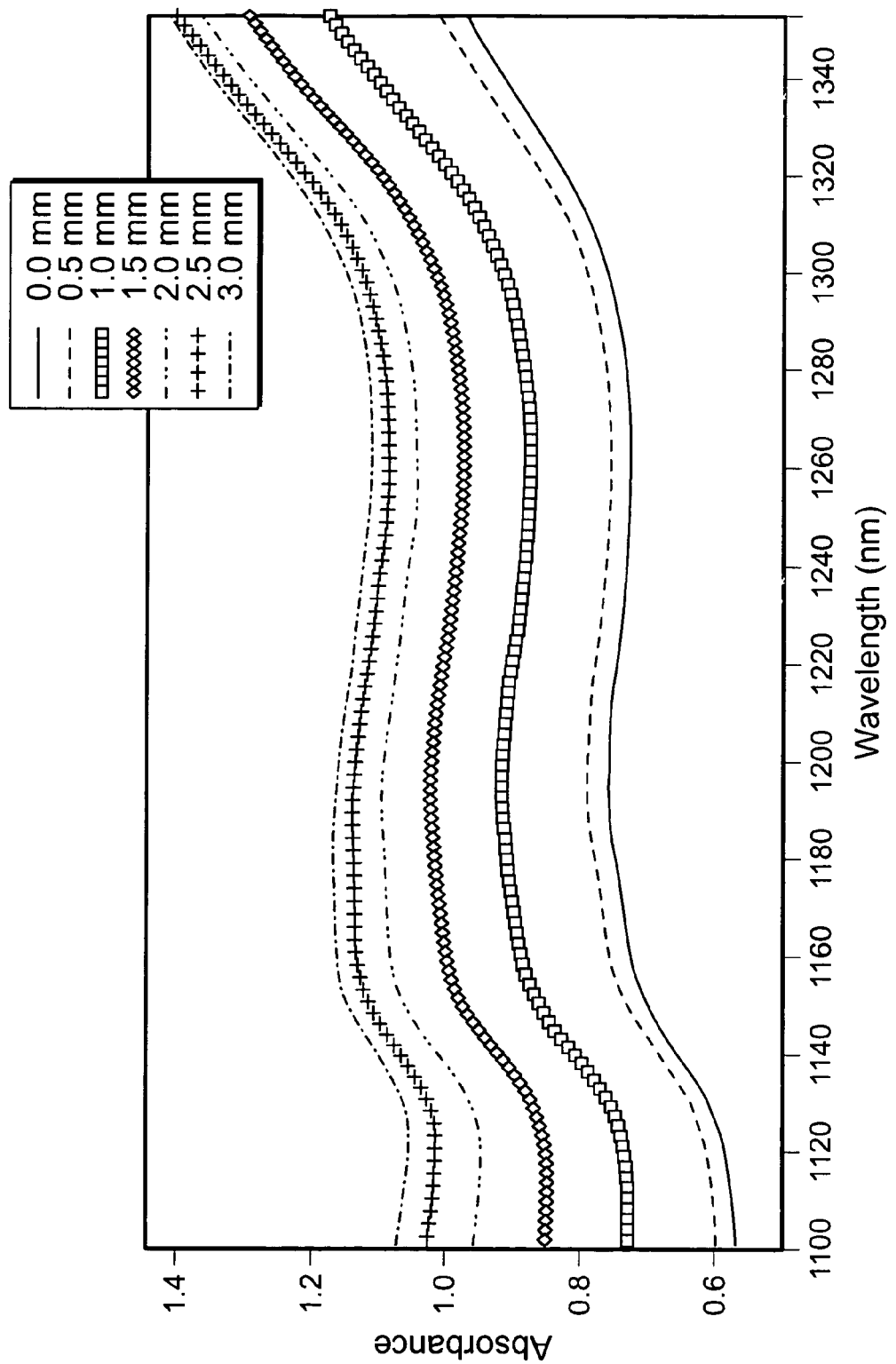
FIGS. 4A and 4B are plots of diseased tissue samples as a function of distance from the top of the tissue to the base of the fiber optic probe spanning eight different tissue-to-probe separations from 0.0 mm to 3.0 mm with blood intervening.
Figure 4B:
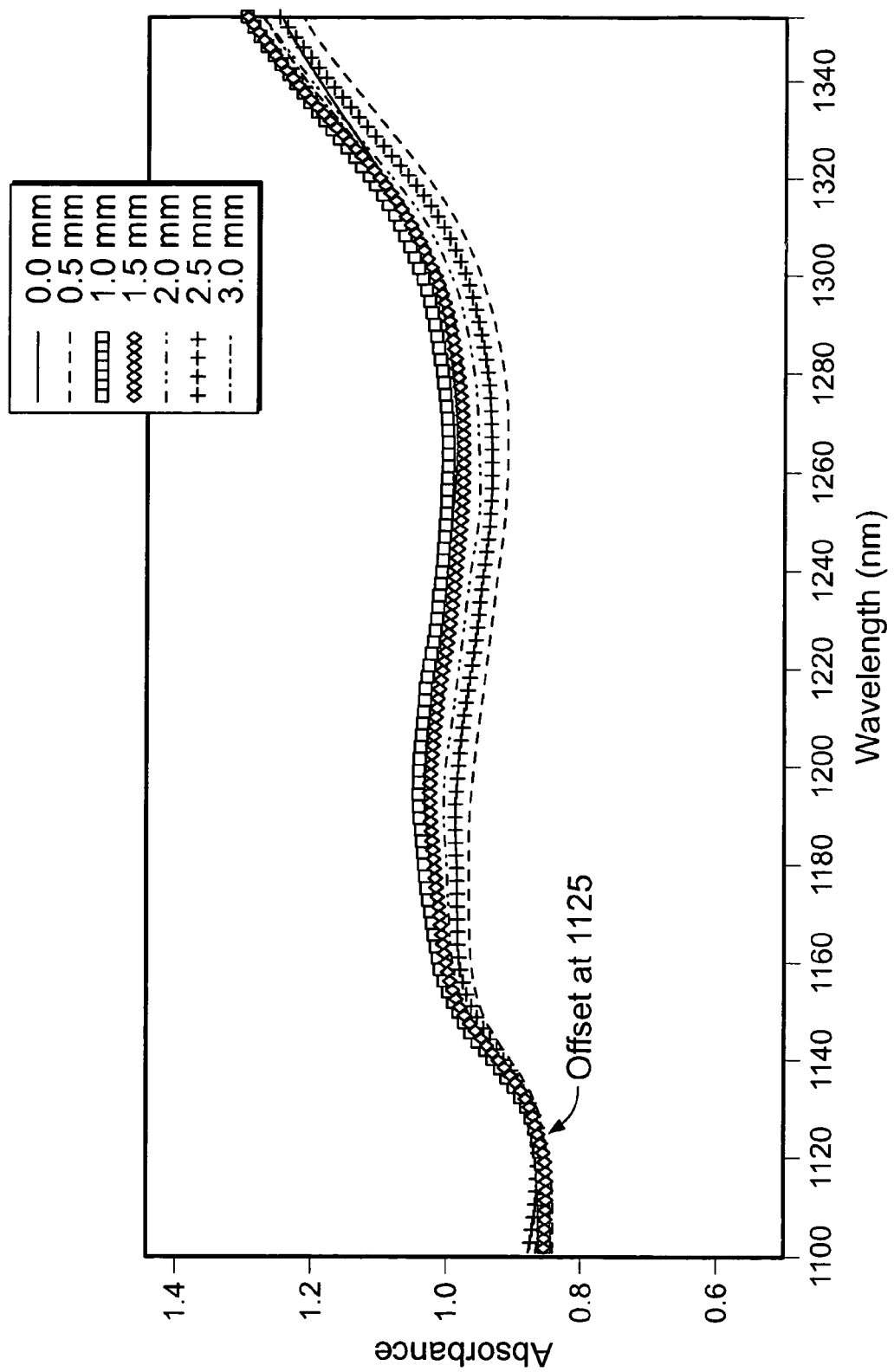

The digital data may be first preprocessed to remove interferants unrelated to the signal of interest, such as the baseline slope, the offset, and/or the linear or multiplicative effects of scattering. The spectral data can also be centered with respect to each other, autoscaled, normalized, etc. to enhance the small spectral features pertaining to the component of interest The benefits of preprocessing are demonstrated in an experiment in which spectra were obtained through bovine blood of four tissue types found in atheromatous human aortas. The absorbance versus wavelength spectra are shown in FIG. 2 from 1100 nm to 1850 nm. Three disease states are represented as a composition of mainly lipid pool, fibrotic, or calcific, with one spectrum of the normal tissue. These diseased states were determined using the histology and pathology analysis and then categorized and separated by the amount of each composition contained in that particular diseased plaque. FIG. 3 shows similar spectra within the smaller wavelength range of 1100 to 14150 nm. Five categories are shown, including calcific, fibrotic, disrupted plaque, lipid-containing, and normal. FIGS. 4A and 4B show spectra of a diseased tissue sample viewed through various depths of sample to probe separations with bovine blood intervening. Plot 4B has been adjusted by removing the offset at 1125 nm from each of the spectra to remove the major differences due to the sample to probe separation. Measurements were made at 0.0, 0.25, 0.5, 1.0, 1.5, 2.0, 2.5, and 3.0 nm from the tissue surface. As the probe moves further away from the tissue surface, the features seen when the probe was pressed against the tissue become much weaker.

The absorbance can be used directly, but as can be seen from FIGS. 2 and 3, there are offsets and slopes that in general confound the information coming from the absorbance related to the chemical composition or tissue type. There are a number of ways to preprocess the spectra to remove these unwanted effects of shifted baselines and slopes from both the instrument and the biological system effects, along with those of scattering from the biological. Such methods include, but are not restricted to, first or second derivatives, normalization, autoscaling, multiple forms of baseline removal, mean centering (MC), multiplicative scatter correction, standard normal variant (SNV), Savitsky Golay smoothing, detrending, OSP, GLS filtering, wavelet filtering, FIR filtering, and combinations thereof, but not limited to these options. The spectra can be untreated, using the raw absorbance measurements, or they can be pre-processed before further data manipulation within the model building application. In one embodiment, the preprocessing option is standard normal variant combined with mean centering. In other embodiments, the preprocessing option is SNV with MC and detrending, or the spectra are pretreated by removal of the central mean (MC-mean centering). In another embodiment, the preprocessing is a Savistsky-Golay smoothing first derivative.

Figure 5:
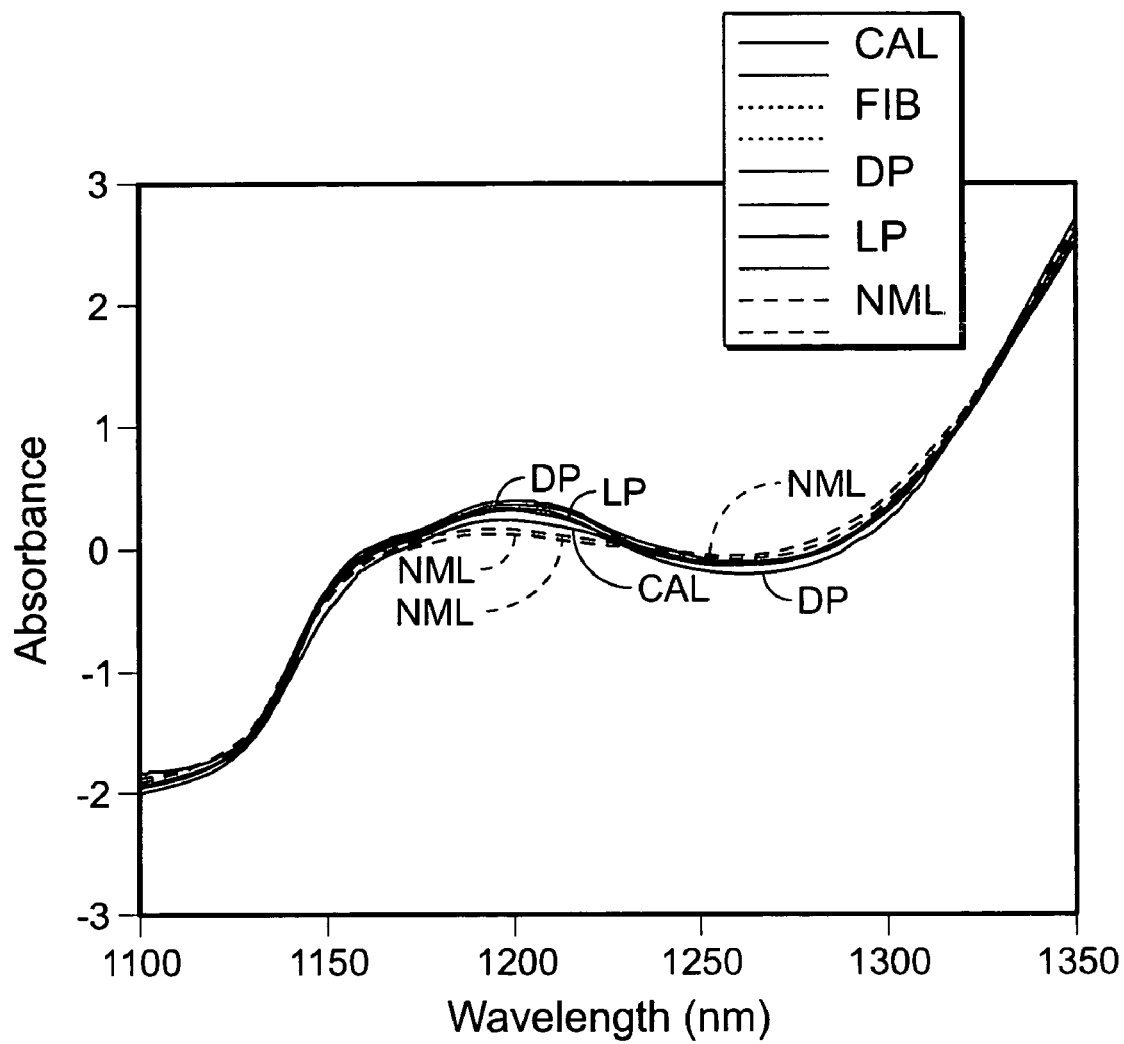
FIG. 5 is a plot of NIR absorbance versus wavelength for the same human aortic tissue samples as those displayed in FIG. 3, but after processing with a standard normal variant (SNV) technique. As shown, the spectra for calcific, fibrotic, disrupted plaque, lipid-containing tissues, and normal tissues, tend to overlap after SNV processing which removed the scattering differences of the samples.
Figure 6:
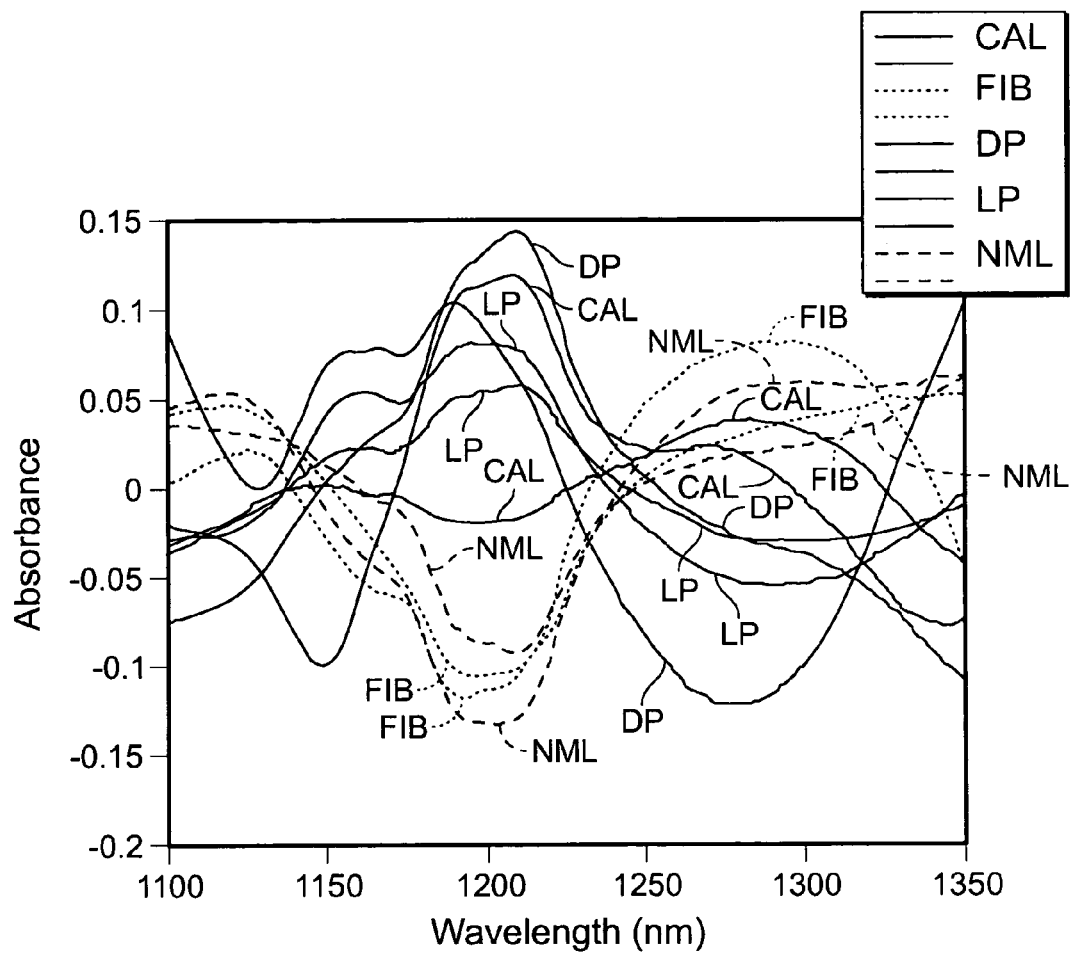
FIG. 6 is a plot of NIR absorbance versus wavelength for the same human aortic tissue after processing with a standard normal variant (SNV) technique as seen in FIG. 5, but the whole group of spectra was further processed by the addition of a mean centering (MC) technique which provides a global mean for all the spectra used to build the model. These techniques when combined indicate where the areas of greatest influence are within the spectral information.

For example, spectra of the specimens shown in FIG. 3 were preprocessed using standard normal variant (SNV) preprocessing. The results are shown in FIG. 5, which clearly demonstrates the successful use of a preprocessing option to remove the scatter between the different diseased tissue spectra, which can otherwise interfere with the process analysis. To further enhance the information contained within the preprocessed spectra, one can use additional techniques. For example, FIG. 6 shows spectra preprocessed with both SNV and mean centering (MC). Comparing FIG. 5 to FIG. 6, it is clear that there are a number of areas within the spectra that vary greatly with the additional preprocessing treatment of MC added to SNV. However, the regions in the spectrum that correspond to the chemical composition of interest within the lesion (in this case lipid pool concentration) are not easily obtained by merely observing the results of the preprocessed data. Thus, the preprocessed digital data is typically processed further to obtain a correlation between the data and the actual constituents within a blood vessel wall, i.e., to determine whether a lesion is vulnerable or safe.

Processing Data

The digital data can be further processed using any or a variety of discrimination algorithms (qualitative analysis) to determine the nature of the correlation between the constituents within the blood vessel walls (as determined by an external means such as morphometry measurements or chemical analysis) and the spectral features obtained in the NIR spectrum (the digital data). In other embodiments discussed in further detail below, one can also make a quantitative analysis of the results.

Useful discrimination algorithms use computerized mathematical models developed by modeling the relationship between spectra and tissue states of known tissue samples. These models are typically based on large amounts of patient data or ex vivo data simulating in vivo data. The mathematical models can be based upon chemometric techniques such as Partial Least Squares Discrimination Analysis (PLS-DA), Principle Component Analysis with Mahalanobis Distance and augmented Residuals (PCA/MDR), and others such as PCA with K-nearest neighbor, PCA with Euclidean Distance, SIMCA, the bootstrap error-adjusted single-sample technique (BEST), neural networks and support vector machines, and other types of discrimination means.

The discrimination algorithm is applied to the digital data from the spectra of an unknown tissue sample in a blood vessel wall to characterize a particular location or point within the tissue. For example, the tissue can be characterized as being part of a lesion or plaque, and if so, whether this is a vulnerable or safe plaque as described above. An output, such as a audible or visual representation, e.g., a graph or other output, can be provided to indicate to the operator the characterization of the vascular tissue, including whether the illuminated blood vessel wall includes a plaque, and if so, whether the plaque is vulnerable or safe, or falls within one of the other categories described above or simply whether the site of illumination contains a plaque that is vulnerable. The output can be based on one or more thresholds, a continuous grading output as described herein, or both types of output in the same system.

Many different types of discrimination algorithms can be used, from the basic form of a simple absorbance comparison between two or more wavelengths, or analysis of large data matrices (raw or preprocessed) with techniques based upon multiple linear regression, Principal Component Analysis (PCA) as described by Malinowski et al, in "Factor Analysis in Chemistry" John Wiley & Sons, New York, 1980. These methods are used to obtain a metric to determine the nature of the diseased tissue from which the groups can be separated.

Figure 7:
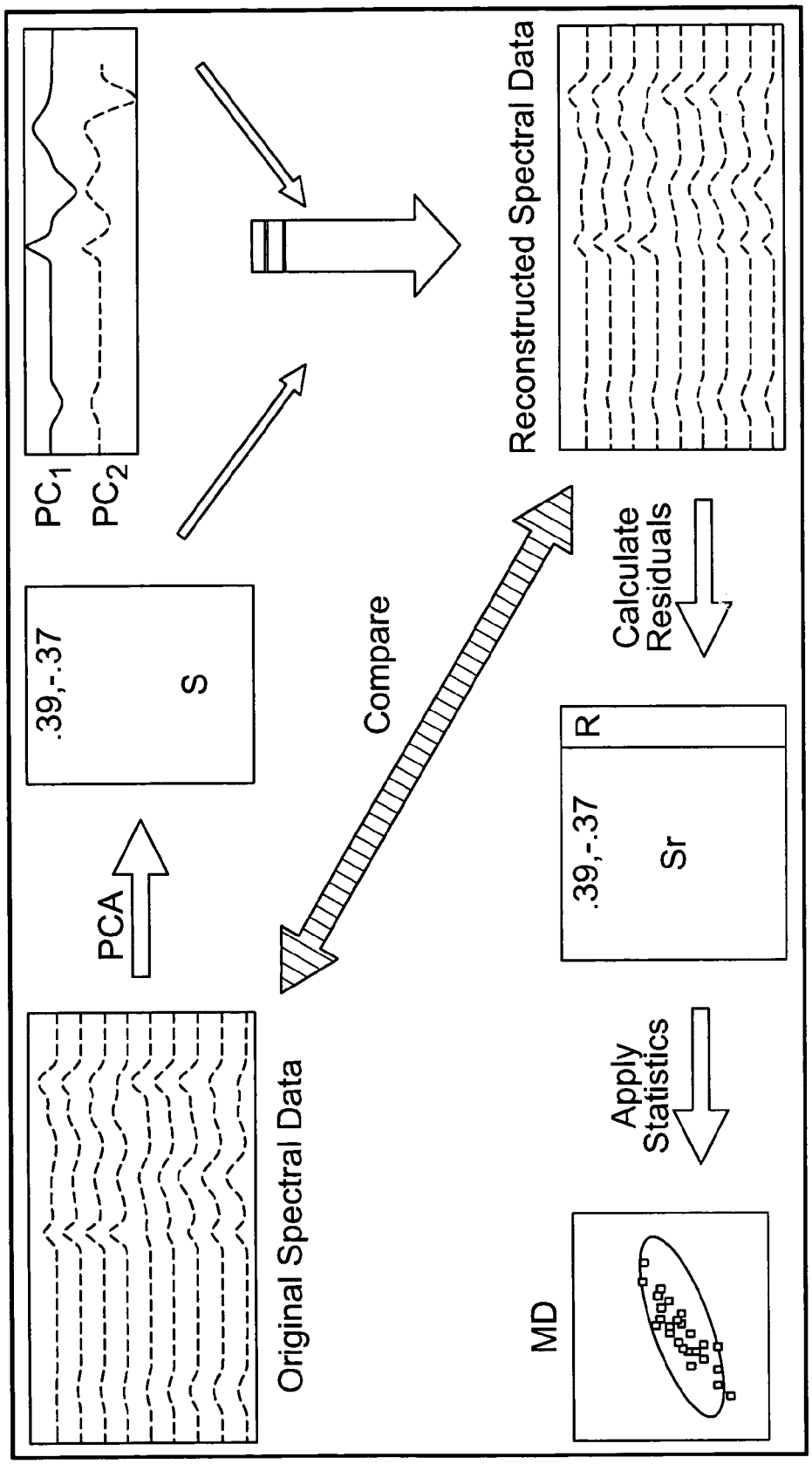
FIG. 7 is a schematic of a processing technique combining principal component analysis (PCA), a spectral decomposition method which breaks the original data into two matrices that contain the Principal Component (PC) vectors and the resultants scalars or Scores (S), coupled with the addition of the spectral residuals (R) to create an appended Scores matrix called Sr, and then applying the non-linear statistics of the Mahalanobis Distance (MD) calculations to the appended Scores (Sr) resulting in a discrimination method termed PCA/MDR.

For example, one embodiment uses PCA, which enables the use of large amounts of spectral data information, which can be decomposed (and therefore compressed) into a matrix of factors (or vectors, principle components, latent variables, eigenvectors, etc.) that retain only the largest variations expressed by all the spectra of the tissue type of interest, and a matrix of the resultant scores (or scalars, eigenvalues, etc.) used to scale the amplitude of each of the factor vectors. The upper half of FIG. 7 is a schematic that depicts the PCA process of spectral decomposition of the original spectrum into the Scores (S) and Principal Component (PC) matrices. As shown in the lower half of FIG. 7, the results are then analyzed by reconstructing the spectra from the combination of the S and PC values and then minimize the difference between the comparison of the original to the reconstructed spectra using the residuals (left over values from the comparison squared and then summed).

In some embodiments, once a metric has been chosen, a threshold is applied to determine the likelihood of whether the unknown tissue spectrum can be classified as a diseased tissue type or not (this is the threshold that is avoided when using a threshold-less system as described herein). Many methods can be used for this determination such as a simple wavelength comparison technique using linear regression lines, or more complex geometries such as Euclidean or Mahalanobis distances as thresholds for more complicated separations. When analyzing large volumes of spectral data, PCA can be used and can also be combined with a variety of metrics for discrimination such as a linear regression line, e.g., such as the one used in the partial least squares-discriminate analysis (PLS-DA) method described in Ericsson et al., "Multi- and Megavariate Data) Analysis: Principles and Applications" (Umetrics Academy, 2001), Euclidean distance, and Mahalanobis distance as described by Marks et al in the following articles: Analytical Chemistry, 57, 1449, (1985); Analytical Chemistry, 58, 379, (1985) and Analytical Chemistry, 59, 790, (1987). Other elements besides the scores of the PCA decomposition can be used for a metric with a threshold, such as the soft independent modeling of class analogies (SIMCA) described in Gemperline et al., *Anal. Chem.*, 61:138, (1989), the bootstrap error-adjusted single-sample technique (BEST) described in Lodder et al., *Appl. Spec.*, 42:1352, (1988), and other discriminatory techniques which use the residual rather than the scores from the reconstructed spectra.

In other embodiments, the original processed data (in the form of a set of numbers, with one number for each point or location within a scanned tissue sample) is continuously graded using standard techniques to provide a scale or value for each point without the use of a threshold. Thus, these methods utilize the raw scores, or the so-called "discriminant" based on the detected radiation, directly to provide a continuous scale, rather than comparing the discriminant to a threshold and providing a "yes/no" or other similar answer based on specific categories.

One embodiment combines the scores of the separate classification groups, determined by spectral decomposition using partial least squares, and applying a threshold determined by maximizing the classification separation between two or more groups to establish the boundary calculations termed the PLS-DA method.

In the embodiment in which a PLS algorithm is used for discrimination analysis (PLS-DA), the scores from the S matrix are used to build the discrimination calibration model. A threshold can then be set to maximize separation of the scores in the model group from those scores of the other group that were used in a binary representation. For predictions, an unknown spectrum is decomposed to the same S matrix, and if the score is above the threshold of the model then the sample is said to be a member of the model class.

In other embodiments of the PLS-DA algorithm, no threshold is needed and the resultant scores are displayed as a continuous grading using a standard technique to provide a scale or value for each point without the use of a threshold. The threshold-less method directly provides a continuous scale, rather than comparing the discriminant to a threshold and providing a "yes/no" or other similar answer based on specific categories.

In one embodiment, the raw PCA scores can also be used. Another embodiment of the model algorithm is a variation of PCA combined with statistics of Mahalanobis Distance (MD), which can be also be augmented with the addition of spectral residuals (R) as described in a similar method developed by Gemperline et al., *Anal. Chem.*, 62:465, (1990) (see FIG. 7) where they combined PCA with SIMCA. This model embodiment, (PCA/MDR), developed by Duckworth, et al. of Galactic Industries and incorporated into their PLSplus/IQ™ Chemometric software uses PCA, SIMCA, and Mahalanobis Distances to determine the maximum discrimination of the model. In still another embodiment, the PCA residuals can be used in the same way as in the method employed in SIMCA.

This model is formed by calculating the Mahalanobis distance on the matrix of the PCA score values from the spectral decomposition augmented with the mean centered sum squared residuals left over from the comparison of the reconstructed spectra to the original spectra used in the model. This matrix is termed (Sr) in FIG. 7 and contains the scores for the description of the maximum variation of the spectra contained in the model augmented with the mean centered summed squared residuals left over from the PCA decomposition. These values are then subjected to the Mahalanobis Distance calculations using the following equation:

$$M = \frac{(Sr)^T (Sr)}{(n-1)}$$

in which M is the Mahalanobis matrix, T indicates the transpose is taken of the Sr matrix, and normalized by n, the total number of spectra that were used to build the model. The Mahalanobis matrix is then used to calculate the Mahalanobis Distance (D) for each Score (i) produced in the model.

$$D_i = \sqrt{(Sr_i) M^{-1} (Sr_i)^T}$$

To make a comparison between all the members of the model, a root mean squared group (RMSG) size is then calculated for the model. This is done by obtaining the sum of all the squares of the predicted distances for each of the samples used in the model ($D_i$) normalized by the number of samples used in the model (n):

$$RMSG = \sqrt{\frac{\sum_{i=1}^{n} D_i^2}{(n-1)}}$$

The final calculation normalizes each of the Mahalanobis Distance ($D_i$) scores by the group normalization factor (RMSG). To determine whether the normalized score values are within the model group or outside of the model group values a boundary is set and in general this boundary is set at 3 standard deviations away. The Mahalanobis Distance is the first metric used to determine if an unknown sample is part of the model group or not.

The final decision as to whether a spectrum from an unknown tissue sample fits the particular model can be made using three metrics: (i) the fit of the unknown residual augmented scores to the Mahalanobis Distance based upon the residual augmented scores of the model, (ii) the resultant residual of the unknown spectrum compared to a distribution test such as a T-test or F-Test of the model residuals, and (iii) a comparison as to whether the unknown score fits within the range of scores used to build the model.

To determine if the unknown sample is part of a specific group or category, the spectrum of the unknown is first preprocessed in the same manner as the model and then decomposed into its PCA components plus residual. The mean residual value obtained from the model is then subtracted from the unknown residual to obtain the Sri value, where (i) represents the residual augmented scores vector for each of the individual unknowns. This value is then applied to the following equation to obtain the Mahalanobis Distance (D) for each of the (i) unknowns:

$$D_i = \sqrt{(Sr_i)M^{-1}(Sr_i)^T}$$

This distance is then divided by the group RMSG value before testing the calculated Mahalanobis Distance of the unknown against the standard deviation of the all the distances obtained from the model. In one embodiment, three standard deviations (3σ) are used for the Mahalanobis Distance boundary of the model. This is the first of three "flags" or indicators used as a disease index to ascertain whether the unknown sample falls within the model group (category) or not. The second flag is obtained from the model residuals. A standard distribution test such as a T-test, Chi-Squared, or F-Test is then applied to the model residuals at some level such as the 99% level, and this value is used to determine if future predicted residuals fall within the model range. The third flag is the comparison of the unknown score to the maximum and minimum score of the model or compared to a standard distribution test such as the T-test, Chi-Squared, or F-Test performed at some level such as the 99% level. If any one of the three flags is not present (false), then the sample is ruled not to fall within the model group/category being tested.

In another embodiment, the threshold is optimized during the model testing stage against a test set of data that represents the lesions or normal tissues that are not part of the diseased state. This optimized threshold is then used instead of the fixed three standard deviations (3σ).

Although the use of thresholds has its benefits, their values are often determined based on in vitro test results that may not accurately reflect in vivo spectral characteristics. Even if a threshold is based on a large amount of in vivo data, a particular patient may not fit within the norms assumed when establishing the threshold. For such a patient, the best "control" may not be a predetermined threshold, but a sample or location of his or her own tissue known to be normal (or at least a safe lesion, if looking for vulnerable lesions). By using a continuous scale to represent the set of numerical data representing the scanned locations within a tissue, e.g., in an artery, the new methods and systems can provide the user, e.g., a physician, nurse, or technician with the opportunity to diagnose the vulnerability of a particular lesion without a threshold, and thus without the risk of an improperly set threshold, which could cause an incorrect diagnosis.

Another advantage of the thresholdless display is that the operator (e.g., physician, technician, or nurse) can make his or her own decisions as to the trade-off between sensitivity and specificity, by applying his or her own categories, criteria, or thresholds (which would otherwise be dictated by the system). The thresholdless display enables the operator to review a variety of discriminant values from multiple locations within a given patient, and compare those values to each other to make a diagnosis.

In some embodiments, the threshold and continuous grading techniques can be used together to provide a double-checking system.

Figure 12A:
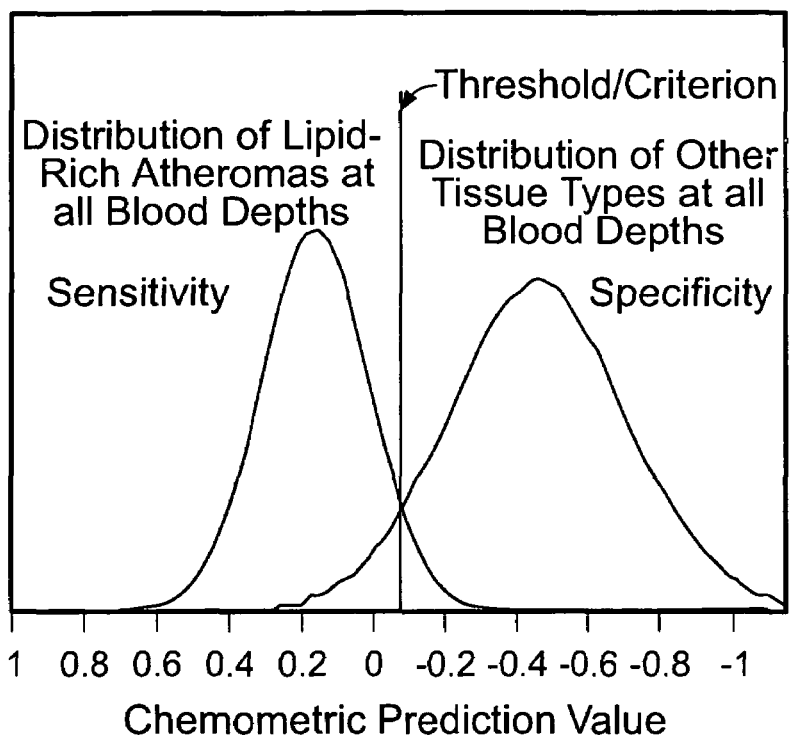
FIGS. 12A and 12B are hypothetical graphs of chemometric prediction values.
Figure 12B:
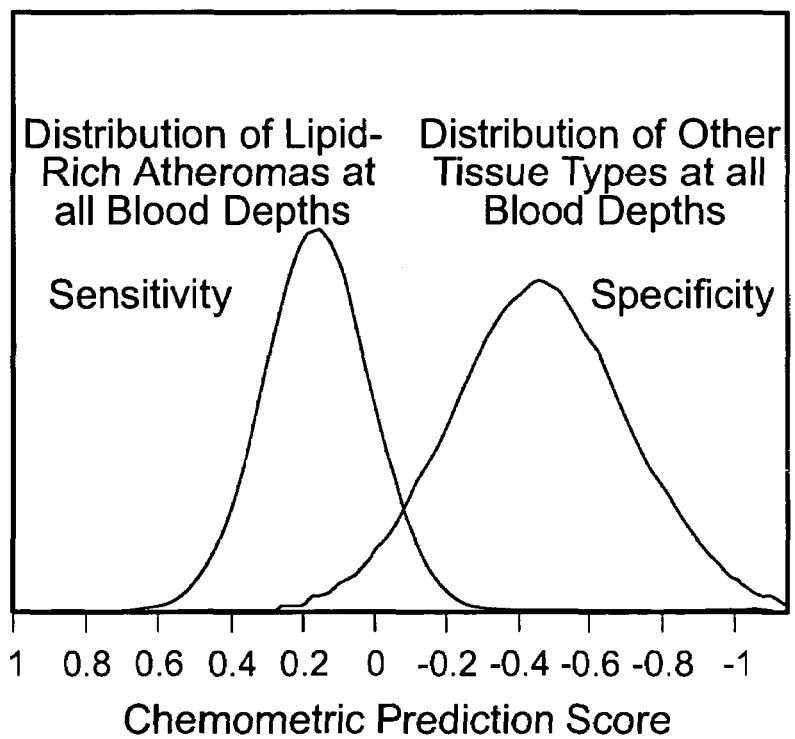

FIGS. 12A and 12B illustrate the differences in the two methods. In the graph in FIG. 12A, a threshold is set to maximize the sum of sensitivity and specificity of this system in which an algorithm reduces the spectrum scanned to a number between −1.0 and 1.0. In this case, we are using the group Mahalanobis Distance as our metric of "scoring," but other metrics may also be used. The peak of lipid-rich atheromas (vulnerable plaques) is at a value of about 0.2. The peak of other tissue types is at about −0.4. The threshold separating the two sets of values is set at about −0.1. Thus, any sample locations having a value greater than −0.1 are designated vulnerable plaques.

FIG. 12B shows the same graph as in FIG. 12B, but without a threshold. Here, the system displays the values directly or by use of a continuous grading system such as false color, a gray scale, or sound. In this system, the operator (e.g., a physician) reviews and interprets the values. Any number between −1.0 and 0.2 could be interpreted as a safe lesion, or a somewhat vulnerable lesion, any number between −0.2 and 1 could be interpreted as a vulnerable lesion, or a somewhat vulnerable lesion. Values located somewhere in the middle can go either way based on the operator's experience and knowledge about a particular patient and/or treatment in view of possible risks of treatment.

Figure 14:
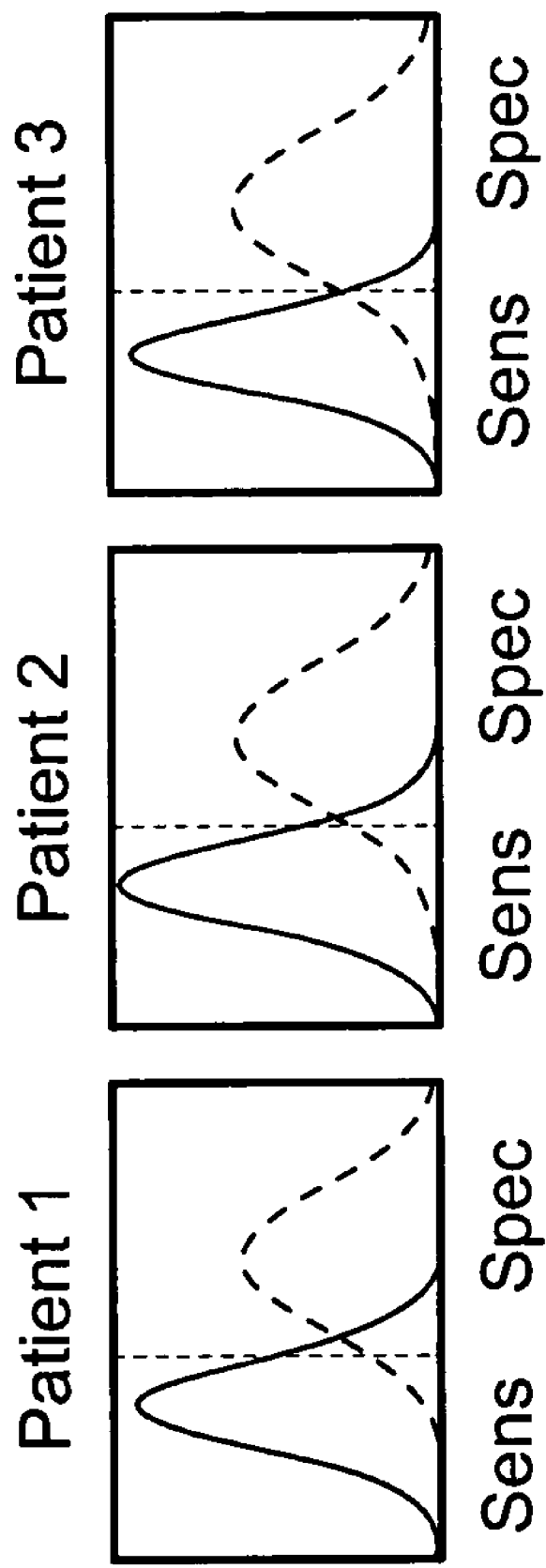
FIG. 14 is a series of graphs showing sensitivity and specificity curves for three different patients. If the same threshold is used for all three patients, some may receive an incorrect diagnosis.

FIG. 14 shows a series of three graphs similar to FIG. 12A, in which each graph represents the results from a different patient. The same threshold is used for each patient, and as the graphs show, a single threshold may not be optimal for all patients because of inter-patient variation. In other words, the reflected radiation in one patient may not mean the same thing in another patient. Displaying the data directly enables the operator to decide upon a patient-specific threshold after taking individual patient considerations into account.

Figure 15A:
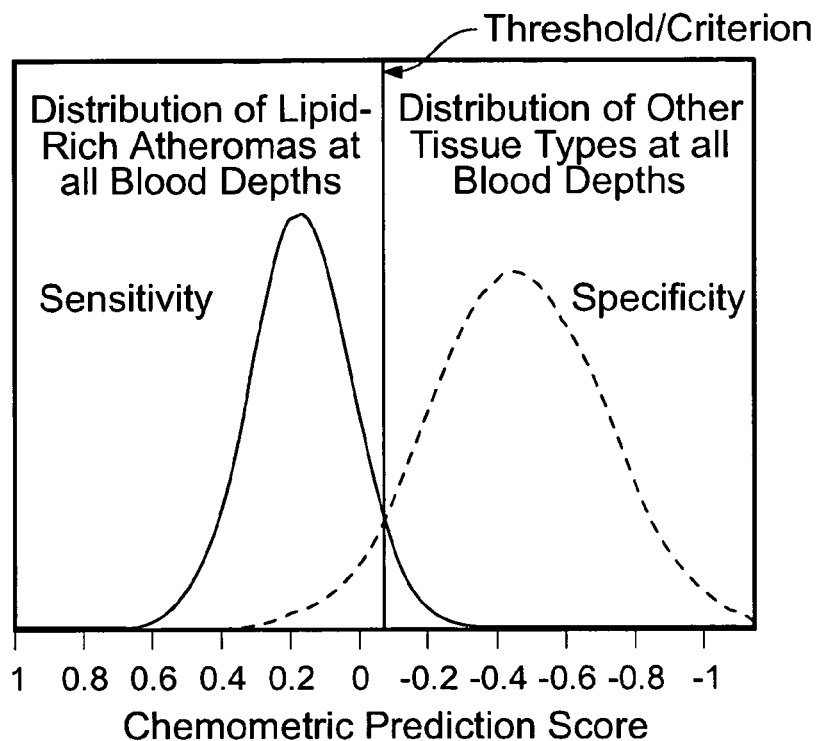
FIGS. 15A to 15D are four different graphs of chemometric prediction scores.
Figure 15B:
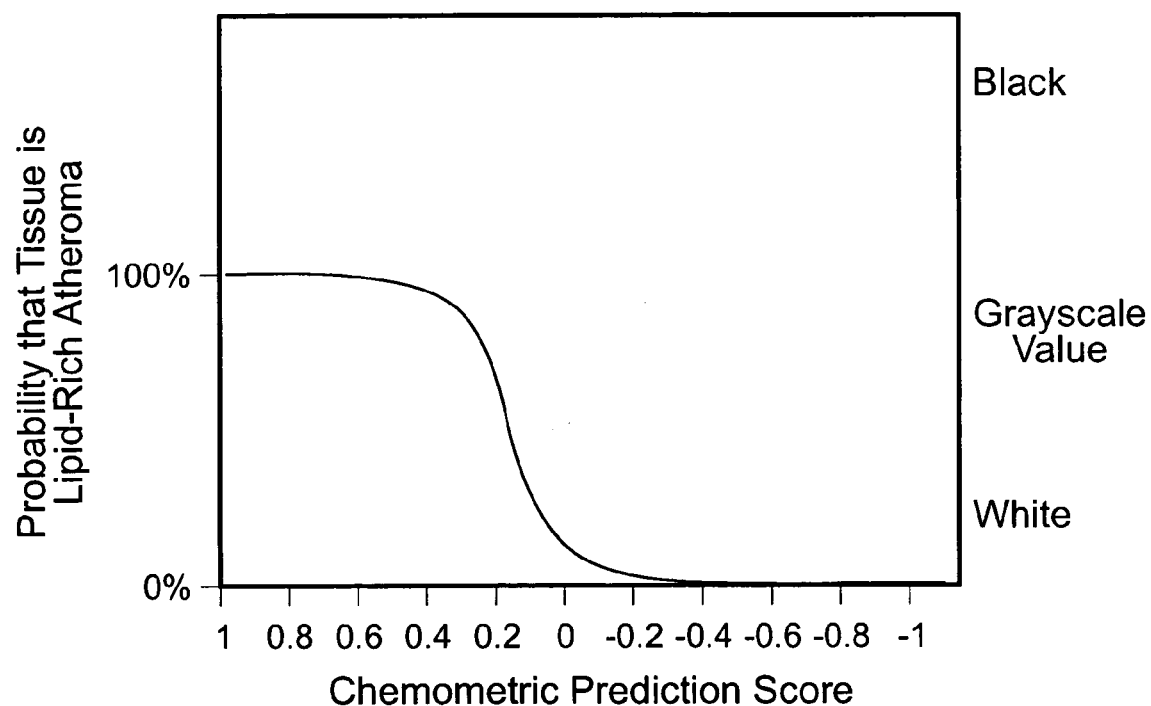

FIGS. 15A to 15D are graphs showing chemometric prediction scores. This "score" can also represent the group Mahalanobis Distance or another metric used to describe the state of the tissue. FIG. 15A is similar to FIG. 12A. FIG. 15B is a graph showing the probability that a given tissue sample is a lipid-rich atheroma. One can calculate the probability that tissue with a given score is in a specific group (such as lipid-rich atheroma vs. all other tissues) from the distribution of chemometric scores of known populations of tissue samples. Such calculations can be made, for example, using a contrast maximization algorithm, and the results can be displayed in a grayscale. For example, one can use white for −1.0 and black for +1.0 (for chemometric scores), where 100% lipid-rich atheroma is black, and 0% lipid-rich atheroma is white. The probabilities can be displayed as an alternative to direct display of the chemometric scores. The probabilities provide more of a visual distinction or differentiation at the overlap between the two tissue distributions in the example shown in FIGS. 15A and 15B. For example, rather than using an entire grayscale to depict values from −1.0 to +1.0, the endpoints and values from +1.0 to +0.4 can be set to black, and values from −0.4 to −1.0 can be set to white. Thus, the grayscale covers only the values between +0.4 and −0.4, thereby providing more visual contrast at these middle values near the threshold.

Figure 15C:
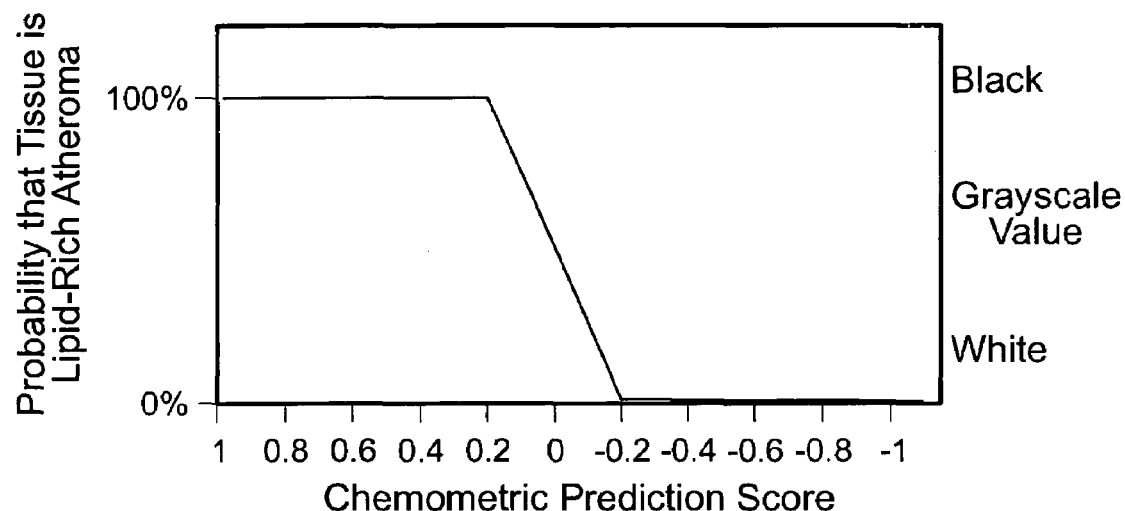
Figure 15D:
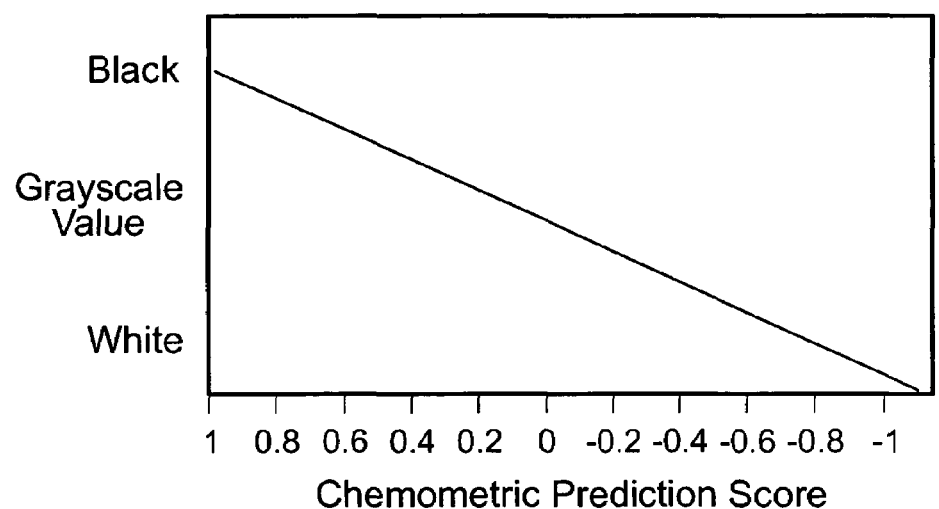

FIG. 15C is a graph similar to FIG. 15B, but shows a straight-line approximation of the curve in FIG. 15B. FIG. 15D is a graph that does not show a probability, but just a grayscale value in a straight line (from 100 to 0 percent) in which every chemometric score is equally important. These figures are just examples, and scalar data can be displayed in various ways known in the art.

Quantitative Analysis

In addition to the largely qualitative analysis discussed above, quantitative analysis can be used to predict the actual concentration of specified chemical constituents retained within a given location of tissue or lesion. For example, spectral information can be directly linked to the actual chemical constituent using a variety of different types of quantitative analysis based upon both univariate and multivariate analysis techniques. Univariate methods include correlating spectral peak heights or areas under the spectral curve to known chemical quantities of interest within the tissue or lesions, using for example least squares regression to develop a quantitative model. Another univariate method includes K-Matrix or classical least squares (CLS), which uses larger sections of the spectra (or the whole spectrum) regressed with respect to all of the chemical components within the spectral region (see, e.g., D. M. Haaland and R. G. Easterling in Applied Spectroscopy, 34, 539, 1980).

To avoid the complications that can arise when using univariate models, such as requiring knowledge of all the concentrations within the region of the peaks (i.e., unknown concentrations will throw the model off), multivariate techniques may be more useful. In one multivariate method, multiple linear regression (MLR) (also termed P-Matrix or inverse least squares (ILS)) is used to build a model using only the concentrations of the chemical components of interest (see, e.g., H. Mark, Analytical Chemistry, 58, 2814, 1986). While this technique allows the model to be built using only the known concentration without any unwanted effects, the model is limited in the number of wavelengths that can be used to describe each of the components.

There are other multivariate techniques that combine the ability to use large regions of the spectra to represent the constituents of interest (like that of the CLS model) with the ability of having to contend with only the constituents of interest (like that of the MLR model). In one embodiment, principal component regression (PCR) is used (as described in Fredericks et al., Applied Spectroscopy, 39:303, 1985). This method is based upon spectral decomposition using PCA, followed by the regression of the known concentration values against a PCA scores matrix.

Another embodiment that can be used to obtain actual concentration values of lesion constituents based upon spectral data involves another multivariate algorithm termed partial least squares (PLS) analysis (see, e.g., P Geladi and B Kowalski, Analytica Chemica Acta, 35:1, 1986, and Haaland and Thomas, Analytical Chemistry, 60:1193 and 1202, 1988). PLS is similar to PCR, however, both the spectral information and the concentration information are decomposed at the start of the method and the resultant scores matrices are swapped between the two groups. This causes the spectral information correlated to the concentration information to be weighted higher within the model.

The core of the PLS algorithm is a spectral decomposition step performed via either nonlinear iterative partial least squares (NIPALS)(see, e.g., Wold, Perspectives in Probability and Statistics, J Gani (ed.)(Academic Press, London, pp 520-540, 1975) or simple partial least squares (SIMPLS) (Jong, Chemom. Intell. Lab. Syst., 18:251, 1993) algorithm.

Figure 16:
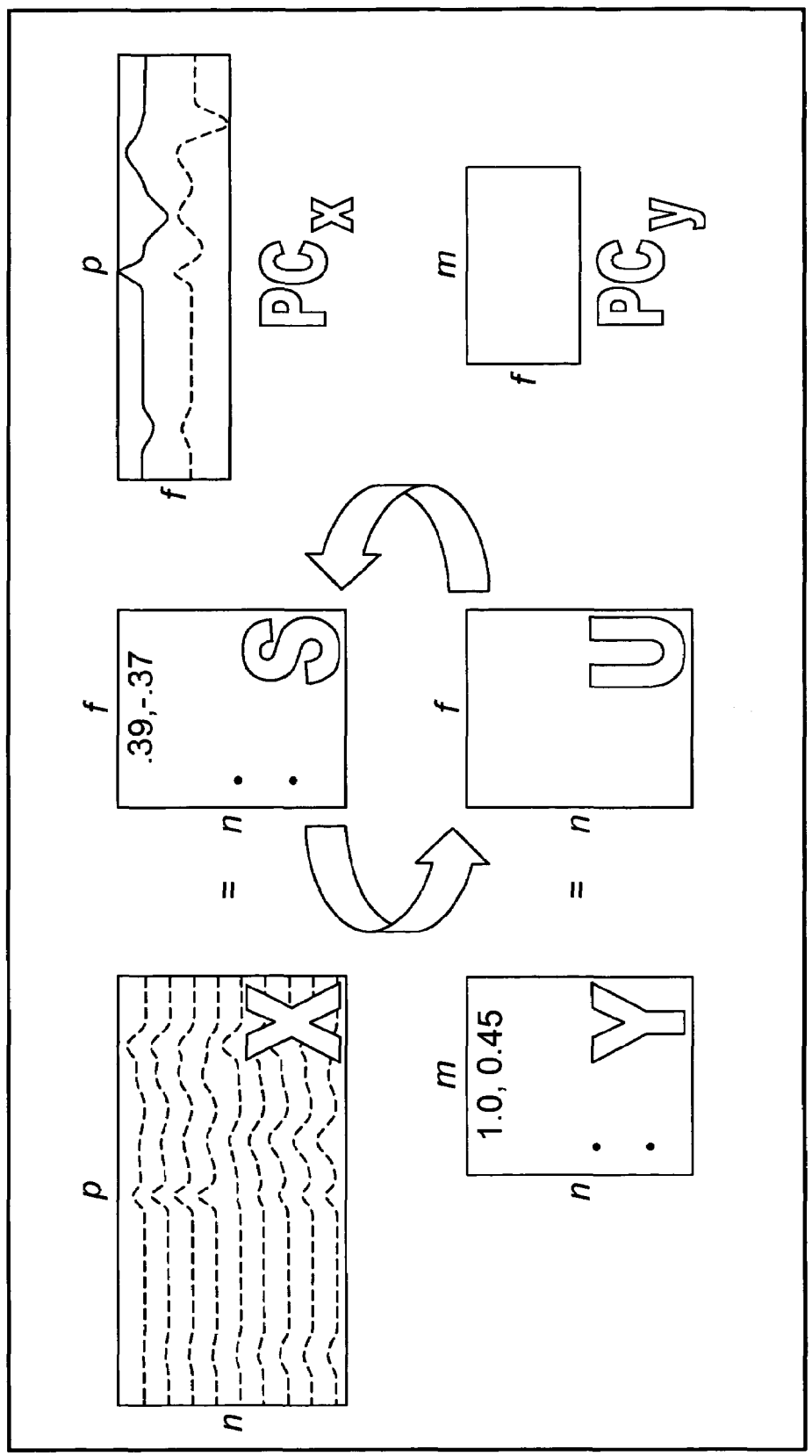
FIG. 16 is a representation of NIPALS decomposition of spectral information represented by matrix X (spectral data) and matrix Y (concentration data).

FIG. 16 is a diagram representing the NIPALS decomposition of the spectral information represented by matrix X containing spectral data and matrix Y containing concentration information (or binary classification information if using this method as a discrimination means). S and U are resultant scores matrices from the spectral and component information, respectively, and PCx and PCy are resultant principal components (or latent variables/eigenvectors) for the spectral and component information, respectively. The other nomenclature in the figure is for the number of spectra (n), the number of data points per spectra (p), the number of components (m), and the number of final latent variables/eigenvectors (f).

Once the first decomposition for the spectral and concentration/constituent data is made, resulting in a latent variable and score for each of the X and Y matrices, the scores matrix for the spectral information (S) is swapped with the scores matrix containing the concentration information (U). The latent variables from PCx and PCy are then subtracted from the X and Y matrices, respectively. These newly reduced matrices are then used to calculate the next latent variable and score for each round until enough PCs are found to represent the data. Before each decomposition round, the new score matrices are swapped and the new PCs are removed from the reduced X and Y matrices.

The final number of latent variables determined from the PLS decomposition (f) is highly correlated with the concentration information because of the swapped score matrices. The PCx and PCy matrices contain the highly correlated variation of the spectra with respect to the constituents used to build the model. The second set of matrices, S and U, contain the actual scores that represent the amount of each of the latent variable variation that is present within each spectrum. It is the S matrix values that are used in the PLS-DA model.

In one embodiment, the PLS method is used to predict that actual compositions of the diseased tissue. For example the PLS algorithm can be used to predict the chemical content directly or for example in the form of a percentage of lipid, fibrotic, calcific, cholesterol, macrophage, and water content within the probe scanning area. In another embodiment the PLS method can be used to predict the pH or temperature of the diseased tissue or blood.

In certain embodiments, direct numbers or percentages can be replaced by ranges or values from the prediction results of ranges for example less than 10%, 11 to 25%, 26 to 40%, 41 to 60%, 61 to 75%, 76 to 80%, and 81 to 100% and other combinations of ranges and values for prediction of lipid, fibrotic, calcific, cholesterol, macrophage, and water content within the probe scanning area. In other embodiments, the PLS method can be used to predict various ranges of the pH or temperature of the diseased tissue or blood.

Another embodiment treats prediction values above a certain threshold as vulnerable (or life-threatening) and below the threshold as safe (or not life-threatening). For example, a vulnerable plaque may be designated as a region that contains 40% or more lipid content, therefore any predictions with respect to the lipid content would then be in the category of vulnerable. Multiple categories can be combined and each assigned a threshold value. If the prediction scores are at or above the threshold values for all the categories, then the result is the sample is considered vulnerable.

Devices for Use in the New Methods

To perform the new methods, an improved apparatus is provided for analyzing lesions and plaques in blood vessel walls in vivo. The apparatus can also be used for in vitro analysis. The new apparatus includes an external radiation source, such as a laser or other NIR radiation source for transmitting the incident NIR radiation within the wavelength range of 1100 to 1350 nm and at sufficient power. This source can provide the desired NIR radiation region by scanning or by generating NIR radiation that spans the wavelength bands described herein. In addition, the source can provide two or more single wavelengths within this range similar to filter based NIR instruments. The radiation can be delivered sequentially or simultaneously. A variety of NIR sources can be used to provide the required incident NIR radiation. For example, NIR spectra can be obtained from human blood vessels, such as the coronary arteries or aorta, using light sources such as tunable semiconductor lasers or solid-state lasers, fiber-coupled systems such as Raman amplifier lasers, or super continuum fiber lasers and other light sources such that the wavelengths can be scanned. Alternatively, the light source may produce spectral bands that enable simultaneous illumination of the specimen with all required wavelengths. Tuning and/or spectral detection must occur rapidly (<1 second) to avoid motion artifacts within the arteries. Monochromatic fixed-wavelength sources such as lasers, LED's, semiconductor diode lasers, DFB, can also be multiplexed to serve as the illumination source for spectroscopic measurement.

Radiation is carried from the NIR source to the blood vessel walls via any of a number of types of fiber optic catheters or probes operatively connected to the NIR radiation source (see, e.g., Tearney et al., U.S. Pat. No. 6,134,003; Crowley et al. (BSC), U.S. Pat. No. 5,588,432; and Colston, et al, U.S. Pat. No. 6,175,669. For example, the catheter can have a single fiber optic core. A radiation directing or focusing mechanism can be mounted to the distal end of the catheter to enable the operator to direct or focus the NIR radiation onto a desired target on a blood vessel wall. The focusing mechanism should be adapted to compress the incident radiation beam from the transmitting catheter onto a small spot on the tissue surface to be analyzed. NIR radiation reflected by the tissue of the blood vessel wall can be directed into a receiving optic fiber or fibers to provide a convenient, cost-effective means for directing the light reflected from the specimen to the spectroscopic measurement device. Additionally, the apparatus includes one or more detectors present at the distal portion of the catheter for rapidly detecting the radiation reflected or scattered back from the blood vessel wall being illuminated.

FIG. 1 illustrates one of several embodiments of an apparatus 10 that can be used to carry out the present invention. Depending upon the specific wavelengths used, the apparatus is optimized in a manner to enhance the performance within those bands. This includes, but is not restricted to, optimizing the optical fiber cutoff range, the reflectivity of director (mirror) substrate, the addition of lenses, the material and other properties of the sheath, and other apparatus items that can be changed to optimize the signal received. More particularly, the apparatus 10 includes a fiber optic probe or catheter, generally designated by reference numeral 12. The catheter 12 has a distal end 14. The distal end 14 of the catheter can also include an optical aperture 16 through which NIR radiation is directed and/or focused (via redirecting and focusing means 15). This aperture can be centrally located or directed to one side of the distal end (as shown).

An optical fiber or fiber optic bundle 20 is located within catheter 12. The fiber optic bundle 20 is operatively connected to a NIR radiation source 30 and detector source 40 (see FIG. 1). The NIR source 30 is particularly adapted for generating multiple (e.g., 2, 3, 4, or more) single wavelengths or a wavelength band of any 1, 2, 5, 10, 15, 20, 30, 40 or more nm within the overall wavelength range of from 1100 to 1415 nm.

An individual NIR radiation detector 40 includes one or more detectors present at the distal portion of the catheter, such as lead sulfide detectors, InGaAs, Silicon, Ge, GaAs, indium antimonide detector cooled with liquid nitrogen, e.g., singly or in an array, for rapidly detecting the radiation reflected or scattered back from the blood vessel wall being illuminated. Catheter 12 is inserted into the patient via a peripheral vessel and moved to the desired target 52 area (lesion) using standard techniques and methods. Then, NIR radiation within the 1100 to 1415 nm wavelength range from source 30 is directed along the transmitting fiber optic bundle 20 to the fiber optic catheter 12. There, the NIR radiation from source 30 is projected as an incident beam 17 through the optical aperture 16 onto a blood vessel wall 51 (incident light beam is depicted in full line arrows).

A significant portion of the incident NIR radiation is projected onto point P of the blood vessel wall 51. The same catheter or probe that illuminates the blood vessel walls is typically also used to collect radiation reflected from the target (the so-called "reflectance spectrum"). For example, as shown in FIG. 1, radiation is reflected back into catheter 12 through aperture 16. The scattered, reflected radiation is shown at dash line arrows 18. Catheter 12 directs the reflected radiation so that it falls upon detector 40 via the radiation redirecting and focusing means 15 and a beam splitter 22.

This reflected spectral information must be processed to obtain useful information. As shown in FIG. 1, detector 40 is connected to a means 42 for preprocessing, processing, and analyzing the detected spectra and producing the analyzed results as a functional color scheme or other method to indicate whether the lesion is included or excluded from the model thereof. Specifically, the analysis is completed over selected wavelength region or regions of the incident NIR radiation directed upon the tissue. Thus, reflected radiation within the wavelength range from 1100 to 1415 nm is analyzed or the 1100 to 1415 nm radiation coupled with radiation in the 1650 to 1780 nm region is analyzed. To achieve this end a computer can be used that includes appropriate analytical algorithms as discussed herein.

Figure 13A:
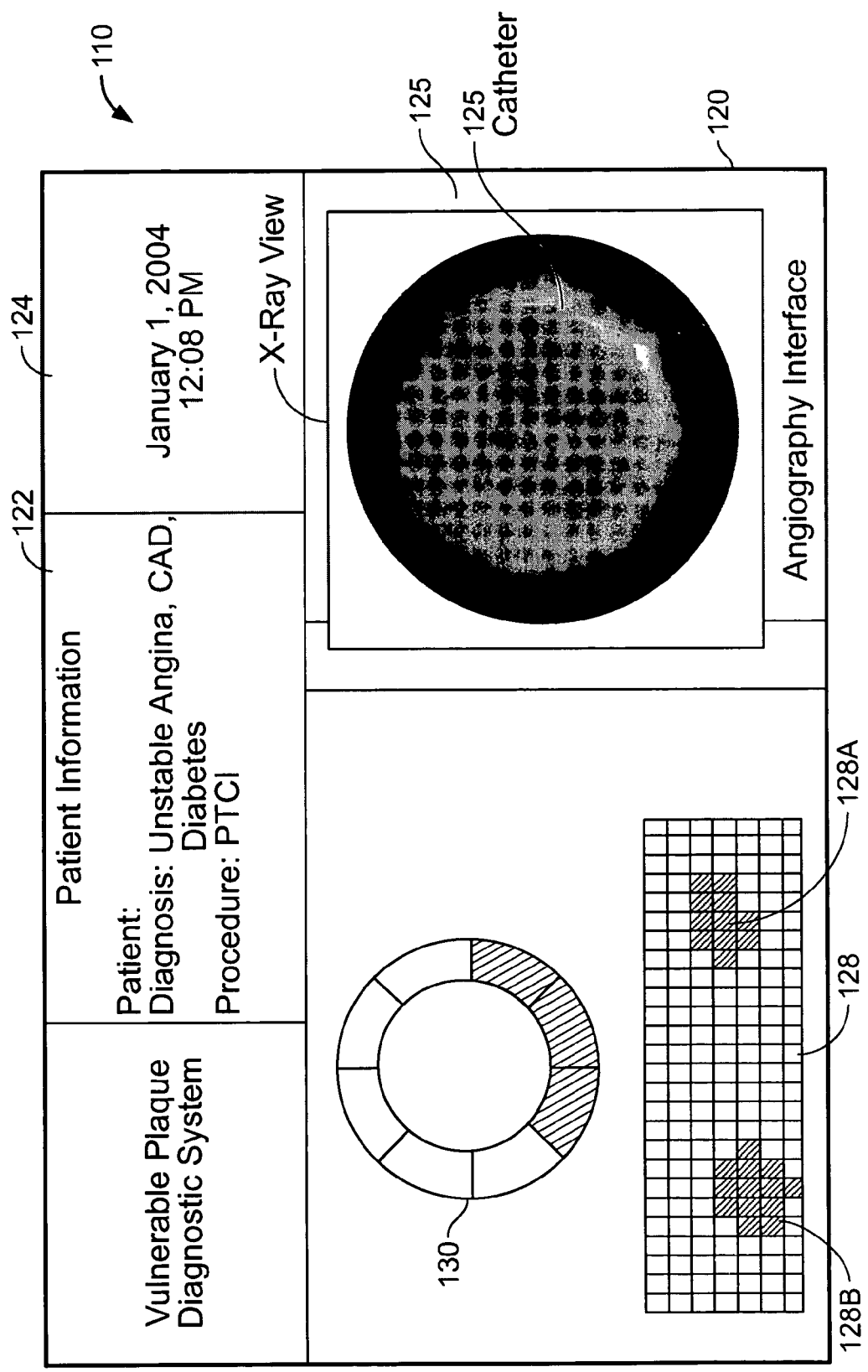
FIGS. 13A and 13B are representations of computer screens showing chemometric data for a vulnerable plaque diagnostic system.

FIG. 13A shows a schematic of a computer screen of a display in a system 110 that uses a threshold. The computer screen 120 shows basic patient information 122, the date and time of a scan 124, and an X-ray view 126 of a catheter 125 within a patient (here in the chest, note the light gray ribs). In addition, screen 120 shows a digitized longitudinal view of an artery being scanned 128, and a digitized cross-section of a particular section of an artery 130. The cross-section 130 is separated into 8 segments, while the longitudinal view of the artery has 7×26 segments (showing an artery sliced longitudinally along the wall and then opened flat).

Because a threshold has been set, the spot at 128a with 11 segments all having the same color or shade of gray indicates a portion of diseased tissue, e.g., a lesion. The spot at 128b has all 13 segments the same color or shade of gray as 128a, indicating another lesion. In cross-section 130, three segments of the "ring" are a light color or light gray, and indicate a lesion. Five segments of the ring are a dark color or dark gray, indicating that the rest of the cross-section is normal tissue free of lesions.

Figure 13B:
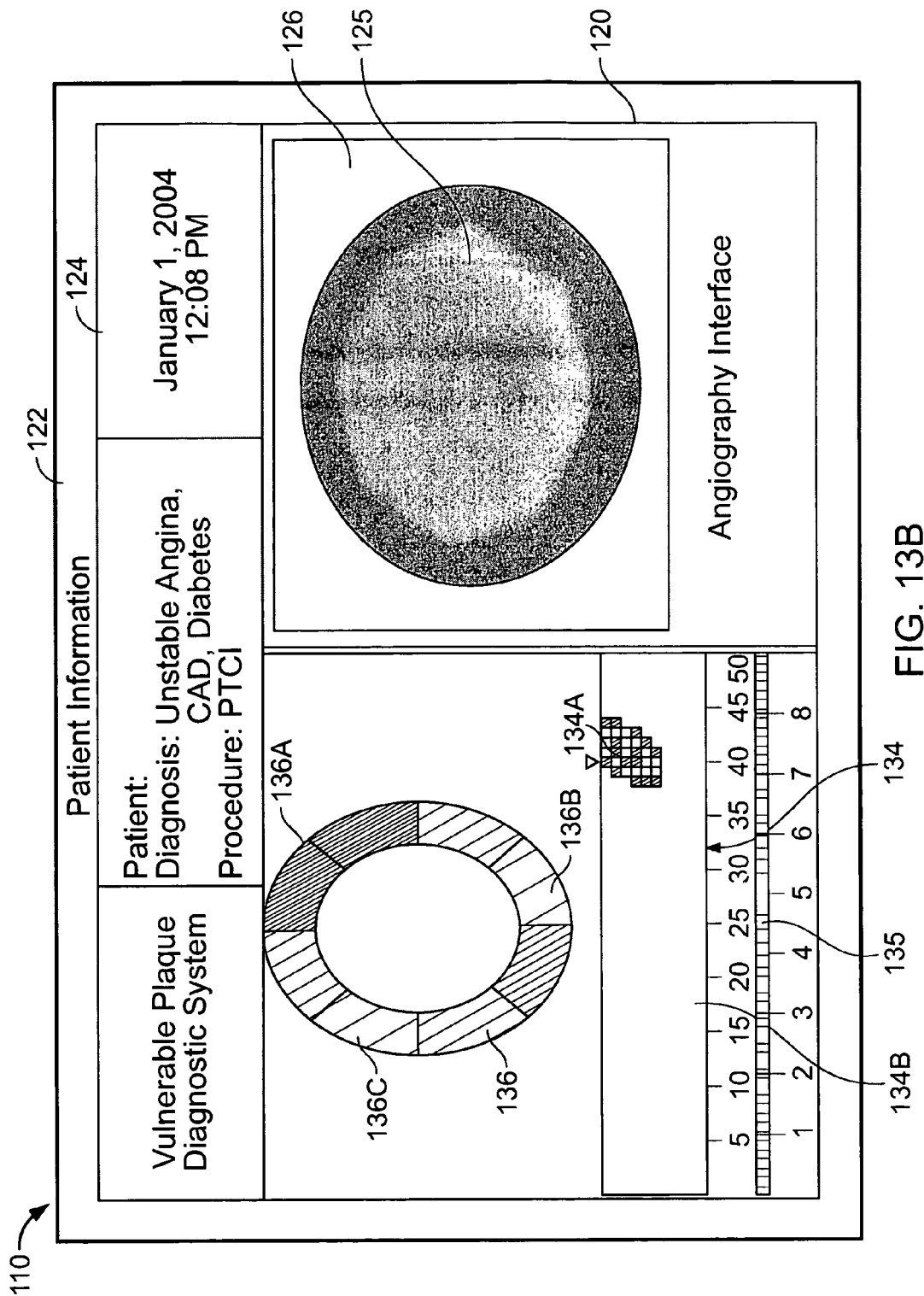

FIG. 13B shows a schematic much like the one in FIG. 13A, but for a system that does not provide or set a threshold. Here, screen 120 shows a digitized longitudinal view 134 having 8×50 segments, and a key or scale 135 to show the colors or shades of gray corresponding to the spectral values. The cross-sectional view 136 has eight segments, but with no two predetermined colors or shades of gray to designate normal or diseased tissue. Instead, cross-section 136 shows a range of colors or shades of gray for different segments of the artery. For example, the segment at 136a is dark, indicating that it is likely to be a safe lesion or normal tissue segment. The segment at 136b is very light indicating a portion of tissue that is diseased, e.g., has a lesion that is likely to be highly vulnerable. The other segments indicate generally healthy segments, with a possible lesion or somewhat vulnerable lesion at segment 136c.

The longitudinal view 134 shows a very light section of about 25 segments indicating a small, but highly diseased portion of tissue 134a, e.g., a highly vulnerable lesion. The rest of the segments being generally darker indicate healthy tissue, with a slightly lighter area of about 30 segments, indicating a possible lesion at 134b, but a fairly safe lesion that should be monitored to see if it progresses into a vulnerable plaque in the future.

To convert a set of numbers, e.g., a range of chemometric values in a set, to a grayscale or color scale, one can use a standard transformation, e.g., a linear transformation, to transform those values to a numerical scale (e.g., 0 to 255 for an 8-bit per pixel display), and then map the chemometric prediction values to a specific grayscale or a color scale using standard techniques. For example, one can use the grayscale ramp from black to white. Black is normally the low end of the range of values, and white is the high end. The map from black to white for each point in a set of values is usually just a linear ramp, for a value (v) which varies from vmin to vmax, the specific gray tone for a given point is then (v−vmin)/(vmax−vmin). For a color map, the most commonly used color ramp is often referred to as a "hot-to-cold" color ramp. Blue is chosen for the low values, green for middle values, and red for the high. One can ramp between these points, or can add the colors cyan and yellow, to provide additional transitions along this linear ramp.

The data can also be plotted in, e.g., a Microsoft® Excel® spreadsheet using a so-called "surface map" charting feature. Commercially available software such as MatLab® also has built-in functions to display an array of data as a grayscale or false color scale.

Experimental Models

The new methods are based upon studies in which NIR spectroscopy was used to examine human aortic samples through whole blood. The samples contained both normal and diseased tissue pertaining to various stages of atherosclerotic plaque growth. The resulting reflectance spectra were converted to absorbance spectra as a function of the log of 1/Reflectance and were analyzed using chemometric techniques that provide a means for modeling the data in such a manner to maximize the spectral information pertaining to the lipid pool content as obtained through blood. Thus, the determination of plaque vulnerability is based, at least in part, on the nature of the lipid pools within atherosclerotic plaques, and their spectral patterns when covered by thicker or thinner fibrous caps.

Computer modeling identified the NIR wavelength range from 1100 to 1415 nm as unique for use in predicting the nature of the lipid pool content in human atherosclerotic plaques. In addition, it was determined that sufficient information could be obtained by illuminating the target tissue with two or more single wavelengths, multiple combinations of single wavelengths or one or more narrow bands of wavelengths, each covering as few as 1, 2, 4, 10, 15, 20 or 30 nm (or up to 100 nm or more), within this range of 1100 to 1415 nm or with a combination of the 1100 to 1415 nm range with the about 1600 to 1780 nm range.

Two chemometric discriminant techniques were used in this study, PCA/MDR and PLS-DA, both based upon PCA, but there are many other discrimination methods that can be used to build the prediction models such as those described above. As discussed above, PCA is a linear regression method that decomposes the spectral information into a smaller set of vectors (principal components, factors, eigenvectors, latent variables, etc.) and scalars (scores, eigenvalues, etc) that describe the variations of the spectral components while leaving out random noise components. Both methods require a training set of representative samples, but differ in the assembly and treatment of those samples. The training set is used to build a mathematical relationship that recognizes similar qualities for a single (or more) classification group, and then the model acts as a screening tool for all subsequent samples tested. The segmentation into the various classification groups was based upon the morphology and morphometry results of the tissue samples. Both discrimination methods are based upon the ability of the samples containing mainly lipid pool (LP) to be distinguished from a combined set of mainly fibrotic tissue (FIB) and calcific tissue (CAL) specimens, and also from normal tissue (NML) through blood.

In the first case, PCA/MDR, the PCA scores from the LP specimen spectra are combined with the remaining noise components (residuals) and a Mahalanobis Distance (MD) statistic is applied to all the scores, obtaining a model based upon the range of the distances that form an ellipsoidal centroid around all the scores (see FIG. 7). Only one group is required to build the model. The other groups are used to establish the relative "goodness of fit" as to how well the model recognizes LP samples and discriminates against the other diseased tissue samples.

Figure 9:
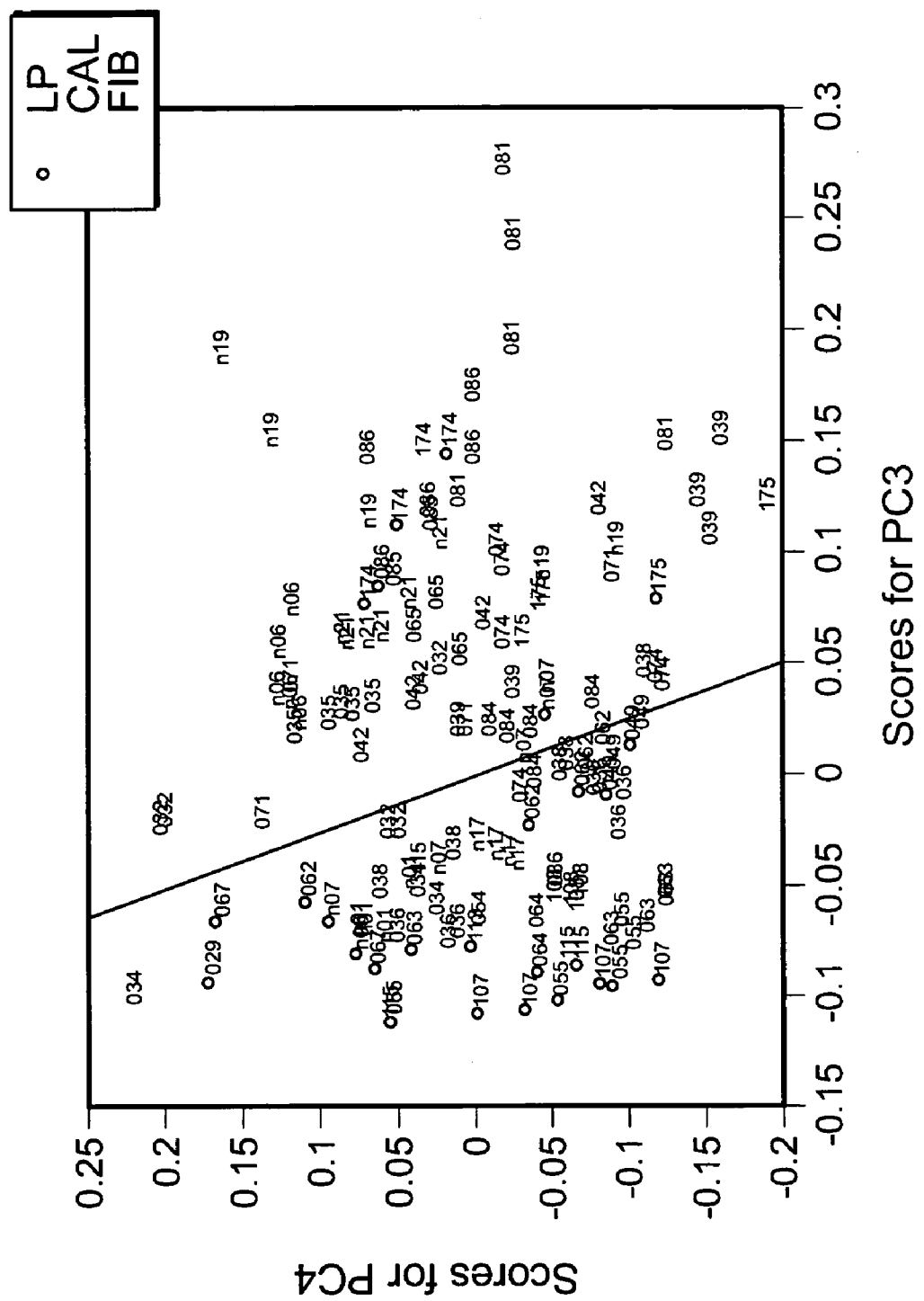
FIG. 9 is a plot of a partial least squares-discriminate analysis (PLS-DA) model of PCA scores between 1100 and 1350 nm. A line is drawn to best separate the scores from the lipid pool samples (LP) from those of all other samples (in this case they were the calcific (CAL) and the fibrotic (FIB) sample scores).

In the second case, PLS-DA, there is a requirement for two groups to be established that are the hardest to distinguish between. These two groups are required to build the model, and the method calculates a "best-fit" line that separates the PCA scores of the LP specimens from the PCA scores of the second group, and in this case the group is the combined FIB and CAL specimen. FIG. 9 is a plot of the results of the PLS-DA model of PCA scores between 1100 and 1350 nm. In this case, a linear discrimination line was used to separate the principal component scores for factor 3 (PC3) from the principal component scores from factor 4

(PC4), where a "factor" is the vector describing the largest influence remaining in the spectral matrix. A best-fit line was drawn to best separate the scores from the lipid pool samples (LP) from those of all other samples (in this case they were the calcific (CAL) and the fibrotic (FIB) sample scores).

To determine how well a model works, separate groups of samples classified by morphology were set aside and used as a validation test set, LP samples not used to build the model were used in the validation step. Sensitivity (SENS) is the ability to recognize a sample that is the same as the model, lipid pool samples in this case and Specificity (SPEC) is the ability of the model to disregard samples that are not the same as the model (NML, CAL, FIB, etc). The reported SENS and SPEC values were comprised of the percentage of the number of LP samples that passed (in the case of SENS) or failed (in the case of SPEC), and in the case of the PCA/MDR model there is a the three parameter tests of the model: (1) the model Mahalanobis Distance boundaries, (2) the score limits, and (3) the residual limits. Both the SENS value and the SPEC values should be close to 100% for the better models, indicating that the model can classify all of the LP samples as LP and reject all other groups tested.

As discussed in further detail in Example 1 below, human aorta tissue samples were analyzed and characterized using standard histology and morphology techniques. As described in Example 2, each sample was subjected to NIR spectroscopy and the resulting reflectance spectra were collected, analyzed, and categorized into large data sets (Example 3).

EXAMPLES

The invention is further described in the following examples, which do not limit the scope of the invention described in the claims.

Example 1

Human Aorta Tissue Sample Preparation

Human aortic tissues were obtained from the thoracic or abdominal region of deceased patients and removed 24 hours or less after death. The tissue samples were stored at 4° C. in saline solution or a phosphate buffered 0.9% saline (PBS) solution. The aortas contained multiple, advanced atherosclerotic lesions unless specifically chosen as normal samples. The aortic fat was removed from the exterior of the aortic vessel. Each specimen (plaque or normal) was removed from the aorta using a 2 cm block template with the plaque or normal region centered within the block and kept moist until the near infrared (NIR) experiments were finished. The plaque sample was oriented such that the maximum lipid pool area was horizontally located in the center of the specimen. Once the NIR spectroscopy experiment was performed, the tissue specimen was placed in a sample holder with the upper left hand corner of the tissue laid in the upper left hand corner of the sample holder. A digital photograph was taken of the entire specimen.

Example 2

Analytical Sample Setup

A NIR spectrum was obtained from each human aortic sample using a FOSS® NIRSystem®, model 6500, with a hand held ½ inch fiber optic probe attachment held in place on a vertical stage adjustment platform. VISION® software version 2.11 data acquisition software was used to collect the spectrum and convert the data from Reflectance to Absorbance units. The recorded wavelength range spanned from 400 nm to 2500 nm acquiring 32 co-added scans at a 10 nm resolution. Data acquisition took 45 second per sample.

Figure 10:
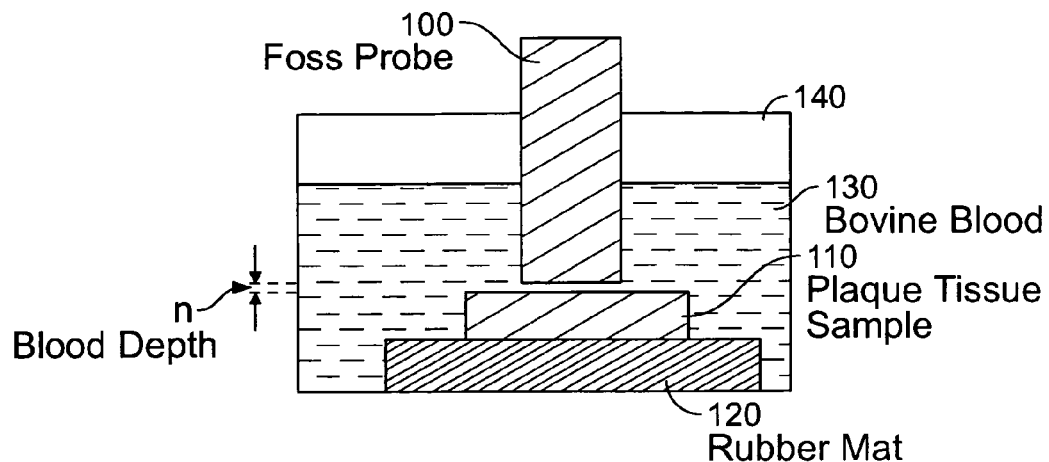
FIG. 10 is a schematic diagram of the NIR spectroscopy experimental setup.

As shown in FIG. 10, an experimental setup was created to hold the fiber optic probe in place at all times during the experiment. A FOSS® probe 100 was located vertically above the plaque tissue sample 110, which is positioned on a rubber mat or pad 120. The sample was illuminated through bovine blood 130. The distance between probe 100 and the sample 120 is the "blood depth n."

A Z-stage micrometer (not shown) was added to the platform to regulate the vertical adjustments of the FOSS probe 100 and to measure the distance from the surface of the sample (zero point) and upwards at 0.25, 0.5, 1.0, 1.5, 2.0, 2.5, and 3.0 mm increments. The specimen was placed on the center of a 4×4×0.5 cm³ black rubber pad 120. The aortic sample 110 with the intimal side facing up was fixed over the rubber with pins at all four corners, and then placed in a small PYREX® dish 140 that holds up to 100 ml of liquid. The sample dish was then placed into a recirculating heated water bath set to 38° C. as monitored by a mercury thermometer.

The optical FOSS® probe was adjusted until it contacted the top of the plaque (or normal) sample and the micrometer was set to zero (0). For each of the probe placements the data acquisition was performed twice without moving the probe. The sample was first scanned in air at the zero mark and then the probe was raised to 2 mm and scanned again. A solution of 0.9% saline (warmed to 38° C.) was then poured into the glass dish immersing both the sample and probe to a height well above 10 mm. The sample was scanned and then the saline was removed using a syringe, without moving the sample or the dish.

Fresh 40% hematocrit bovine blood anti-coagulated with heparin (warmed to 38° C.) was placed in the PYREX® container up to a height of about 15 mm. The probe was lowered back to the zero position (0 mm on the micrometer) and the sample was then scanned in the bovine blood. The probe (using the micrometer) was moved to 0.25 mm and the sample was again scanned, the process repeated for 0.5, 1.0, 1.5, 2.0, 2.5 and 3.0 mm distances between the probe tip and the tissue sample.

All the digital data files were converted from Reflectance to Absorbance and then stored. All of the NIR spectra were visually inspected for data consistency using the VISION® software. Certain data sets were then excluded from further use based on 1) all spectra within a data set did not change with respect to the depth changes, and 2) some samples within a data set changed with respect to depth and other did not.

The results are shown in FIG. 4A, which displays a lipid pool plaque sample at various sample-to-probe distances. FIG. 4B is a plot of the same data shown in FIG. 4A, but the data was offset (normalized) by the absorbance at 1125 nm for each spectrum, showing differences that exist between the samples.

Example 3

Morphological and Morphometric Analysis to Create Data Sets

After processing by NIR spectroscopy, the samples were fixed overnight in a 3% formalin solution. Samples that showed gross evidence of calcification were decalcified in 5% HCl in formalin for 4 hours following formalin fixation.

Figure 11:
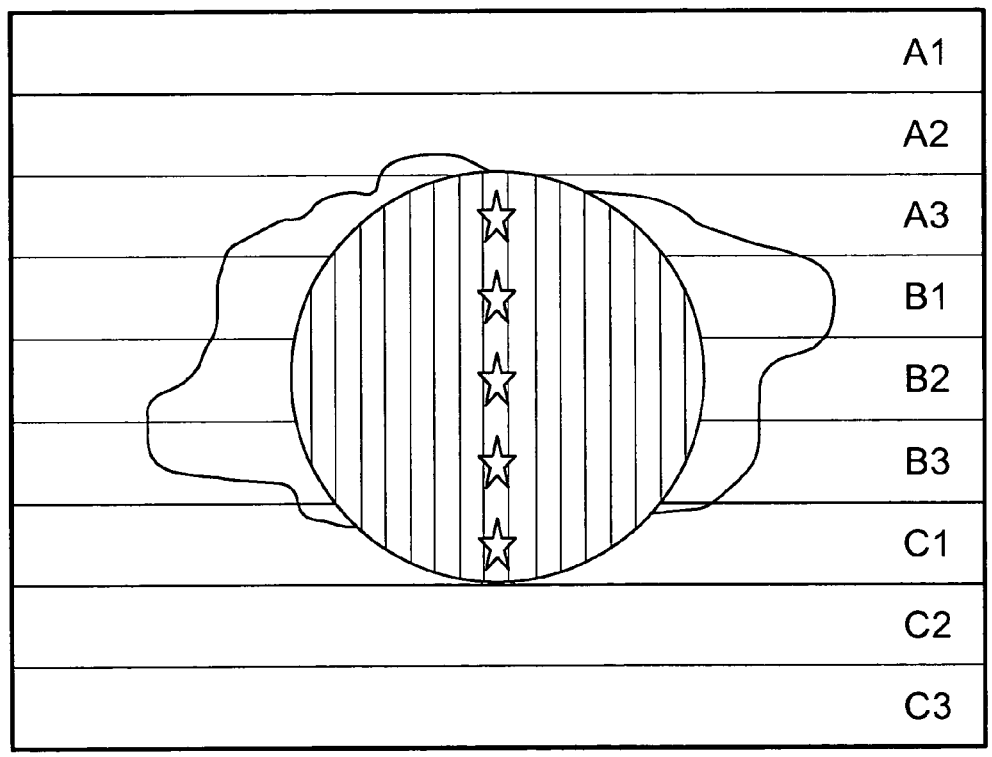
FIG. 11 is a schematic diagram of the histology layout used for processing the tissue specimen. Nine segments were sliced by hand (labeled A1 through C3) with the segments subtended by the FOSS® probe illumination circle (center circle) of most importance (segments A3, B1, B2, B3, C1) in the analysis. The stars indicate the approximate center of each of the segments where the slices for slides were taken to avoid edge effects from the gross cutting.

Sectioning of the specimens was done by hand with a scalpel into three segments, and those three segments were divided (again by hand) into three subsections and placed within paraffin for sectioning. The slides were made from the approximate middle of the subsections at 500 to 750 microns into the block. For the suspected plaque lesion samples, several ribbons were taken from the following subsections: the centermost piece, and the four edge pieces that touch the center piece. FIG. 11 is a schematic diagram of the histology layout used for processing the tissue specimen. Nine segments (labeled A1 through C3) were removed, with the segments subtended by the FOSS® probe illumination circle (center circle) of most importance (segments A3, B1, B2, B3, C1) in the analysis. The stars indicate the approximate center of each of the segments from which the slices for slides were taken to avoid edge effects from the gross cutting. For the normal specimens only the center, and two outer pieces were analyzed (see FIG. 11, segments A3, B2, C1).

Five slides were made for staining purposes, two using H&E and two using Trichrome—Elastin and one spare blank slide. There were 25 slides for each plaque sample and 15 slides for each normal sample. One staining set was produced for planimetry analysis using all the slices, and another set was made for initial morphology analysis using only the centermost B2 slices.

The morphology (or overall description) for each specimen was characterized from the histology of the stained slides for each of the subsections. Within each slide subsection, only the area illuminated by the FOSS® probe was considered in the analysis (see central circle in FIG. 12). The probe diameter was ½ inch (1.27 cm), but the actually projection area used for histology was approximated as a 1 cm diameter circle within the center of the tissue sample to approximate tissue shrinkage and light scattering events during the NIR analysis.

The initial morphology of the samples was performed based upon accepted descriptions of normal and vulnerable plaque tissues established by Virmani et al at the Armed Forces Institute of Pathology (AFIP) Arteriosclerosis. Thromb. Vasc.Biol., 2000, 20:1262. Plaque samples were further separated into lipid pool, fibrous, or calcific plaques with the extremes being classified as having the majority of the main constituent within the probe illumination area. Approximate lipid pool width and depth along with average and minimum cap thickness were also recorded for most of the lipid pool samples.

Computerized morphometry (planimetry) was performed for all the stained tissue slices. The morphometric analysis was used to determine the Total Plaque Area (subtended by the FOSS probe) then separated out into Total Lipid Pool Area, % Lipid Pool Area to Total Plaque Area, and Cap Thickness (measured at the thinnest region only). Further, cap thickness measurements were obtained for all the data samples that contained lipid pools. The average cap thickness was measured over the center 10 mm of the centermost section to provide an average cap thickness value.

The normal samples were also analyzed to determine if the tissue of the outer subsections were free of disease. Any start of disease or lipid pool found in the segments disqualified the specimen as normal. The normal samples were from individuals that ranged in age from as young as 29 up to 87 years of age. Most of the normal samples came from individuals that did not have any disease.

Samples selected for the study represented the diseased plaques of LP, FIB, or CAL along with the NML tissue, all within the FOSS probe subtended area. The LP samples selection was based upon the size of the total plaque area (only the larger plaques were used to build the model) and the ratio of the mean Cap Thickness to the percentage of LP area and the percentage of the LP area to total plaque area (smaller caps on larger LP plaques were ranked as good LP extreme samples).

Example 4

Data Set Development

A subset of the fall data set was formed using the histology analysis as described in Example 3.

The data was segmented out by the two pathologists and then classified as extreme classification samples. The extremes were classified as consisting predominately of one disease component, without regard to the thickness of the cap on the lesion. The full dataset contained a total of 207 samples with 194 usable. The files used for modeling were chosen using two criteria: (i) being in the top ⅓ largest plaques in the sample set, and (ii) the average cap thickness (in microns), in a ratio to the percent lipid pool area to the total diseased plaque area. This threshold was set to be less than 18, determined as the middle of the histogram plot of all the data. This filter process resulted in a total of 33 extreme plaques and 27 Normal (NML) samples. The plaque samples were further classified as 16 Lipid Pool (LP), 8 Calcific (CAL), and 9 Fibrotic (FIB).

To increase the number of plaque samples in the model, 2 lipid-filled disrupted plaque (DP) samples were added to the calibration set and another 2 lipid-filled DP samples to the validation set. This increased the number of LP samples to 10 samples per each set, validation, or calibration. These DP plaque samples were chosen because they were large in size, had very thin to non-existent caps, and still retained a large amount of pooled lipid within the plaque.

Example 5

Determination of the Wavelength Range of 1100 to 1415 nm

The final method used to evaluate the data sets was the linear regression model based upon the Mahalanobis Distance and the scores from the PCA decomposition, the PCA/MDR method. Within the different regions tested, most predictive regions were found to cluster in the region from about 1100 to 1415 nm, and more particularly from about 1150 nm to 1350 nm, about 1175 to 1280, and about 1190 to 1250 nm. The data were first preprocessed for scatter removal using Standard Normal Variant (SNV) with Mean Centering (MC). Overall the SNV with MC preprocessing option provided the best SENS and SPEC results for all models tested as compared to no preprocessing, mean centering, first derivative, second derivative, and other preprocessing options tested. The best band regions found for the dual 30 nm test were from 1175 nm to 1205 nm combined with 1310 nm to 1340 nm, and 1145 to 1175 nm combined with 1250 to 1280 nm. 88% of the LP samples fit the model first model with 86% of the FIB and CAL samples, and 100% of the NML samples were rejected by the model. For the second set of bands, 90% of the LP samples fit the model and 86% of the FIB and CAL samples, and 86% of the NML were rejected by that model.

Specifically, the PCA/MDR model was used to determine the range of configurations that could be used for discriminating plaques containing mainly lipid pool from other disease types and also non-disease types. A minimum of two selected wavelengths or one or more narrow wavelength bands (e.g., one wavelength and one narrow band) within the wavelength range of 1100 to 1415 nm are required. Either continuous or discontinuous wavelengths or regions can be used to build the model without restriction to size. Many PCA/MDR models were made using the data files for the specimens containing mainly lipid pool and discriminated against fibrotic and calcific lesions together, and then the normal tissue, while also encompassing the variations of the spectra as seen through blood as the probe is progressively moved away from the tissue. The assessment of the models that were tested were obtained from the prediction results of all the plaque types, with a tissue to probe separation value from 0.0 mm to 3.0 mm (see FIG. 4), which represent the expected range of distances between the examination device and the tissue being examined in vivo. Larger distances can also be examined.

The calibration model testing process was repeated eight times with randomly chosen lipid pool samples each time. Each repeated calibration process was averaged over all the regions tested providing the Mean Performance results. These results are displayed in the "projection plots" in FIGS. 8A to 8C for model spectra that were preprocessed using Standard Normal Variant (SNV) and Mean Centering (MC). From those results, the regions from 1100 nm to 1415 nm and a combination of bands from the 1100 nm to 1415 nm region in conjunction with bands in the about 1650 nm to 1780 nm regions (e.g., 1650 to 1730 nm) resulted in many useful models. Each model prediction result was captured as the number of the test lipid pool samples predicted to be part of the model (i.e., vulnerable plaque), and the number of calcific and fibrotic, and then normal tissue samples (i.e., safe plaque), that were excluded from the model, and reported as Percent Sensitivity and Percent Specificity1 and Percent Specificity2, respectively.

Figure 8A:
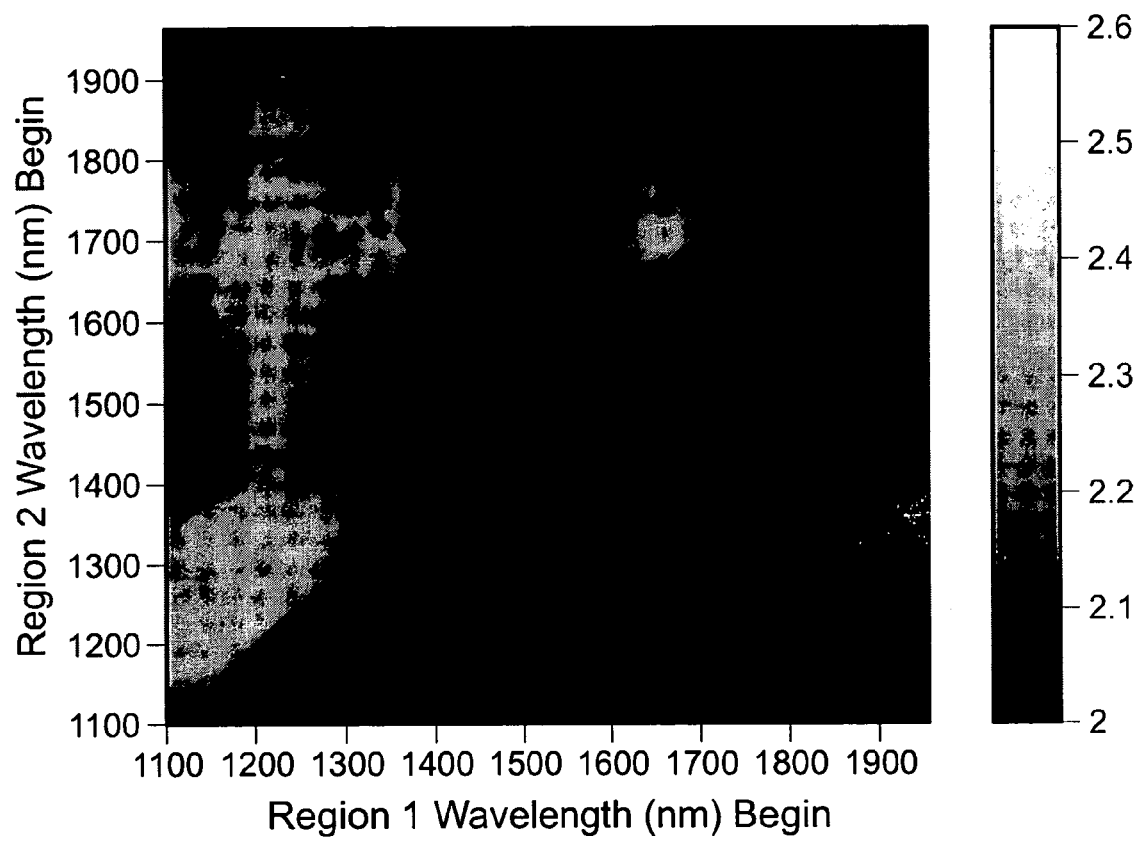
FIG. 8A is a "projection plot" representing the mean prediction performance results from multiple calibration models using two separate 30 nm band regions and preprocessed using SNV plus MC. Specific areas of high Mean Performance occur in the lighter shaded areas and in particular in the regions from 1100 nm to 1415 nm.
Figure 8B:
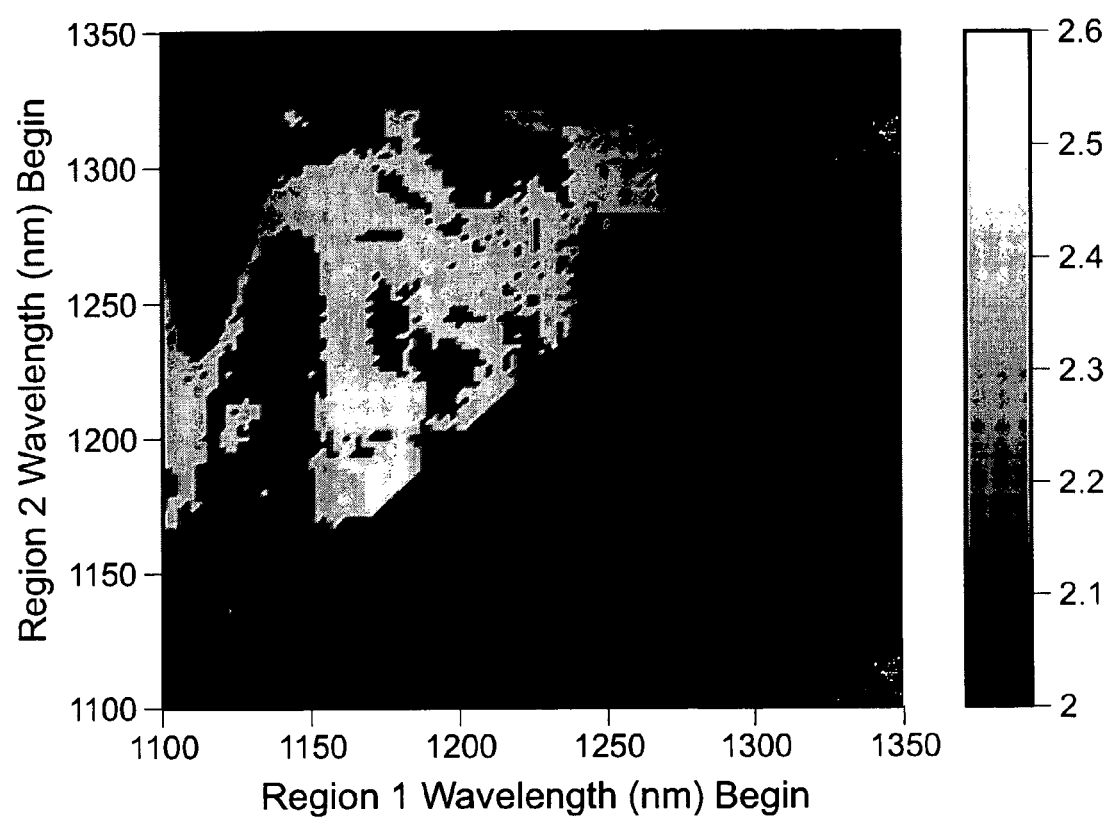
FIGS. 8B and 8C are two additional projection plots of the mean performance using two separate 30 nm bands as in FIG. 8A, but tested at a higher resolution of 2 nm intervals and spanning the region from 1100 nm to 1350 nm. The highest Mean Performance for FIG. 8B occurred in the lighter shaded areas and in particular in the region from 1150 nm to 1250 nm, and for FIG. 8C, the region spanned from 1175 nm to 1280 nm.
Figure 8C:
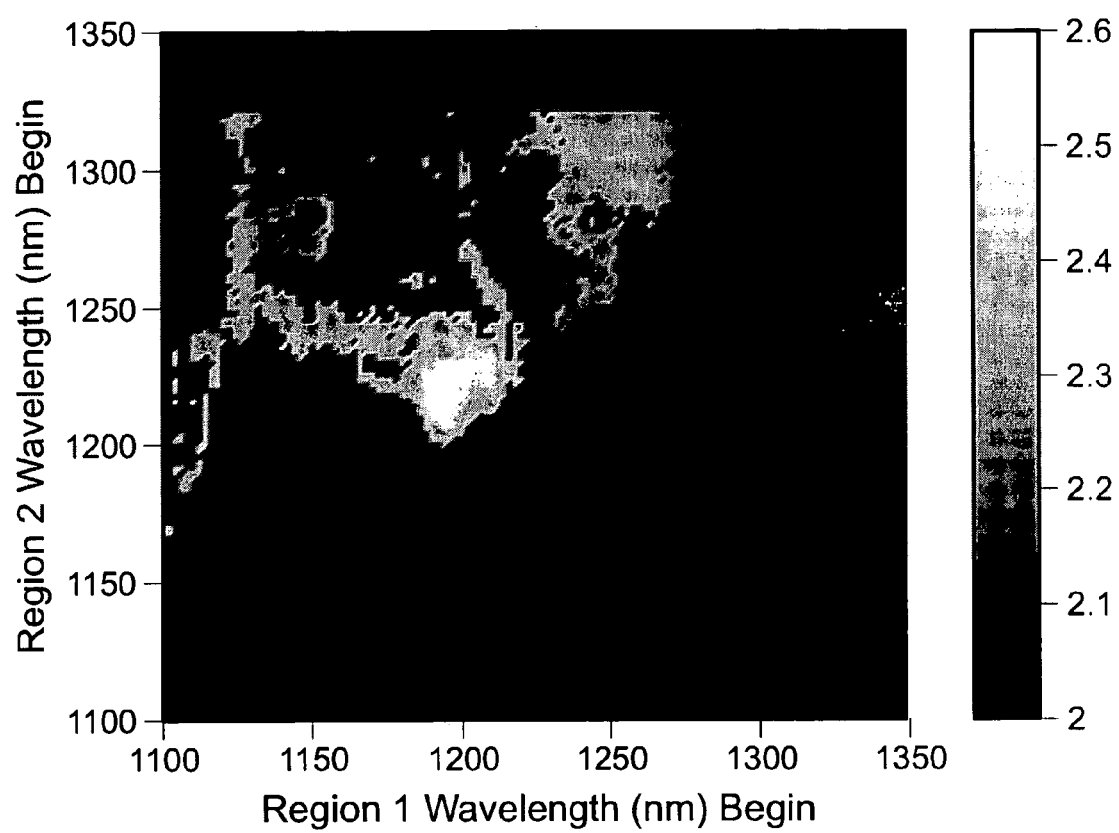

These results were combined as a single metric to generate FIGS. 8A to 8C, in which the x-axis plots the beginning value of the first 30 nm window region and the y-axis plots the beginning value of the second 30 nm window region used in model.

To generate FIG. 8A, two moving "windows" of 30 nm each were tested spanning from 1100 nm to 1850 nm at 15 mm intervals. The X-axis plots the beginning value of the first 30 nm window region and the Y-axis plots the beginning value of the second 30 nm window region used in the model. Only those results greater than 1.8 (equivalent to a minimum response of 60% sensitivity with respect to lipid pool samples not used to build the model, 60% specificity with respect to calcific and fibrotic samples combined, and 60% specificity with respect to the normal samples) were retained. The best result would be 3.0 corresponding to 100% sensitivity and specificity for all groups. Specific areas of high Mean Performance occur in the lighter shaded areas and in particular in the regions from 1100 nm to 1415 nm, and more particularly, 1100 to 1350 nm. Areas of higher Mean Performance occur in the most lightly shaded (highlighted) areas and in particular in the region from 1190 nm to 1250 nm.

FIGS. 8B and 8C are two projection plots of the mean performance using two separate 30 nm bands as in FIG. 8A, but tested at a higher resolution of 2 nm intervals and spanning the region from 1100 nm to 1350 nm. The X-axis plots the beginning value of the first 30 nm window region and the Y-axis plots the beginning value of the second 30 nm window region used in model. A higher threshold was applied to this data (compared to FIG. 8A) so that only those models where the minimum retained value for sensitivity with respect to lipid pool samples was 70%, for specificity with respect to calcific and fibrotic samples combined was 70%, and for specificity with respect to the normal samples was 70%. The best result would be 3.0 corresponding to 100% sensitivity and specificity for all groups and the minimum would be 2.1.

In FIG. 8B, the data was first pretreated using a Savitsky-Golay smoothed first derivative followed by mean centering, and in FIG. 8C the data was first pretreated using Standard Normal Variate with mean centering. The highest Mean Performance for FIG. 8B occurred in the lighter shaded areas and in particular in the regions from about 1150 nm to 1250 nm, and for FIG. 8C, the region spanned from about 1175 nm to 1280 nm.

For example, one embodiment uses two 30 nm band regions that are discontinuous in the region from 1190 nm to 1290 nm as seen in FIGS. 8B and 8C by the grey areas within the very light white region from 1190 to 1290 nm. Another embodiment uses bands from 1175 to 1205 nm with 1310 to 1340 nm. Alternatively, another embodiment uses bands from 1145 to 1175 nm with 1250 to 1280 nm.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for rendering an image of selected tissue on the basis of spectral data, the method comprising
    scanning a series of points within the selected tissue with radiation;
    detecting radiation reflected from the selected tissue;
    obtaining spectral data from the reflected radiation;
    processing the spectral data to generate a set of numbers,
        wherein each number in the set of numbers characterizes a different point of selected tissue,
        wherein each number is indicative of a probability that a portion of a selected tissue belongs to a particular class, and
        wherein the portion of selected tissue is located at the point characterized by the number;
    defining a band having first and second end points corresponding to first and second values of the probability;
    defining a continuous grade output having a beginning value, an ending value, and a set of values between the beginning and ending value;
    determining that a number associated with a first portion of the selected tissue lies outside the band;
    representing the first portion using an end point of the continuous grade output;
    determining that a number associated with a portion of the selected tissue lies within the band; and
    converting the number into a continuous grade output value between the beginning value and the ending value, the continuous grade output value being selected to correspond to the location, within the band, of the number that characterizes the portion of the selected tissue; and representing a portion of an image corresponding to the portion of the selected tissue using the continuous grade output value;

whereby, for each portion of the image, the value of the continuous grade output used to generate that portion of the image is indicative of the probability that a corresponding portion of selected tissue that is classified as belonging to a particular class does, in fact, belong to the particular class.

2. The method of claim 1, wherein representing a portion of an image comprises representing a portion using a color from a false color scale.

3. The method of claim 1, wherein representing a portion of an image comprises representing a portion using a sound characteristic selected from the group consisting of different tones, different pitches, and different volumes of sound.

4. The method of claim 1, wherein scanning a series of points within the selected tissue with radiation comprises scanning the series of points with near-infrared radiation.

5. The method of claim 1, wherein converting the set of numbers into a continuous grade output value corresponding to the location, within the probability band, of the number that characterizes the portion of the selected tissue comprises selecting a number that characterizes the selected tissue by the constituent concentrations within the selected tissue.

6. The method of claim 1, further comprising defining the particular class to be vulnerable plaque.

7. The method of claim 1, wherein representing a portion of an image comprises representing a portion of an image using a shade of gray from a gray scale.

8. The method of claim 1, further comprising selecting the first end point on the basis of spectral data obtained from control tissue obtained from the same patient as the selected tissue.

9. The method of claim 1, further comprising selecting a sensitivity for determining that the selected tissue belongs to a particular class; and selecting the first end point on the basis of the selected sensitivity.

10. The method of claim 1, wherein defining the band having first and second end points corresponding to first and second values of the probability comprises selecting the first and second end points to be chemometric prediction values.

11. The method of claim 10, further comprises selecting a particular probability and selecting at least one of the chemometric prediction values on the basis the particular probability.

* * * * *

UNITED STATES PATENT AND TRADEMARK OFFICE
CERTIFICATE OF CORRECTION

PATENT NO. : 7,376,456 B2  Page 1 of 1
APPLICATION NO. : 10/635330
DATED : May 20, 2008
INVENTOR(S) : Barbara J. Marshik-Geurts, Jing Tang and Andres F. Zuluaga It is certified that error appears in the above-identified patent and that said Letters Patent is hereby corrected as shown below:

On the Title Page, Item (56), under the heading "U.S. PATENT DOCUMENTS" please add the following:

2006/0106293  05/2006  Fantini

On the Title Page, Item -56- "OTHER PUBLICATIONS" please replace the third entry with the following amended text:

Cassis et al., "Cardiovascular Near-Infrared Imaging" http://www.pharm.uky[[⁁]].edu/ASRG/wave/cardiovascular_near-IR.html, 9 pages, (2001).

On the Title Page, Item -56- "OTHER PUBLICATIONS" please replace the fifth entry with the following amended text:

Jaross et al., "Determination of cholesterol in atherosclerotic plaques using near infrared diffuse reflection spectroscopy" *Atherosclerosis* [[~~147~~]] 147:327-337 (1999).

In column 30 lines 20-24, please replace claim 11 with the following amended text:

11. The method of claim 10, further comprising selecting a particular probability and selecting at least one of the chemometric prediction values on the basis of the particular probability.

Signed and Sealed this

Twenty-second Day of July, 2008

JON W. DUDAS
*Director of the United States Patent and Trademark Office*